United States Patent [19]

Scott et al.

[11] 4,251,655

[45] Feb. 17, 1981

[54] SUBSTITUTED N-IMINOMETHYLPIPERIDINES

[75] Inventors: Malcolm K. Scott; Chris R. Rasmussen, both of Ambler, Pa.

[73] Assignee: McNeilab, Inc., Fort Washington, Pa.

[21] Appl. No.: 77,206

[22] Filed: Sep. 20, 1979

Related U.S. Application Data

[63] Continuation-in-part of Ser. No. 10,209, Feb. 8, 1979, abandoned, which is a continuation-in-part of Ser. No. 891,419, Mar. 29, 1978, abandoned.

[51] Int. Cl.³ .................. C07D 211/68; C07D 211/70
[52] U.S. Cl. .................. 542/415; 542/423; 542/424; 546/192; 546/203; 546/205; 546/232
[58] Field of Search .................. 542/424, 415, 423; 546/192, 203, 205, 232

[56] References Cited

U.S. PATENT DOCUMENTS

| | | | |
|---|---|---|---|
| 2,651,023 | 10/1952 | Erickson | 542/424 |
| 3,189,648 | 6/1965 | Gerstovich | 546/229 |
| 3,542,853 | 11/1970 | Peissker | 542/424 |
| 3,657,346 | 4/1972 | Duerr | 542/424 |
| 3,678,109 | 7/1972 | Knowles | 542/424 |
| 3,697,505 | 10/1972 | Gubitz | 260/239 B |
| 3,890,318 | 6/1975 | Obendorf et al. | 542/424 |

FOREIGN PATENT DOCUMENTS

1545603  8/1969  Fed. Rep. of Germany ........... 546/229

OTHER PUBLICATIONS

Seckinger, Helv. Chim. Acta 56 (1973), pp. 776–794.
Zinner et al., Archivo der Pharmacie 299(3), pp. 245–253.

*Primary Examiner*—Arthur P. Demers
*Attorney, Agent, or Firm*—Geoffrey G. Dellenbaugh

[57] ABSTRACT

Substituted N-iminomethylpiperidines are disclosed which are useful for the inhibition of gastric acid secretion.

36 Claims, No Drawings

SUBSTITUTED N-IMINOMETHYLPIPERIDINES

RELATED APPLICATIONS

This application is a continuation-in-part application of our copending application Ser. No. 10,209, filed Feb. 8, 1979, now abandoned, which in turn is a continuation-in-part of our application Ser. No. 891,419, filed Mar. 29, 1978, now abandoned.

BACKGROUND OF THE INVENTION

Unsubstituted N-iminomethylpiperidine is disclosed in U.S. Pat. No. 2,615,023, but said compound does not inhibit gastric acid secretion even at doses four times or greater than those at which the subject compounds are active. It has now surprisingly been discovered that certain substituted N-iminomethylpiperidines are effective inhibitors of gastric acid secretion.

SUMMARY OF THE INVENTION

Description of the Compounds

The present invention comprises substituted N-iminomethylpiperidines of Formula (I):

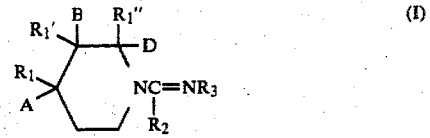

wherein:

$R_1$ taken individually is a member selected from the group consisting of hydrogen; phenyl; phenyl substituted with from one to three members each selected from the group consisting of loweralkyl, loweralkoxy, hydroxy and halo; phenyl($C_1$-$C_4$)loweralkyl; 1-phenyl($C_7$-$C_9$)loweralkyl; phenyl($C_1$-$C_4$)loweralkyl and 1-phenyl($C_7$-$C_9$)loweralkyl in which said phenyl is substituted with from one to three members each selected from the group consisting of loweralkyl, loweralkoxy, hydroxy, halo, and phenyl, provided that no more than one member is phenyl; diphenyl($C_1$-$C_4$)loweralkyl; diphenyl($C_1$-$C_4$)loweralkyl wherein at least one of said phenyls is substituted with from one to three members each selected from the group consisting of loweralkyl, loweralkoxy, halo, hydroxy, and phenyl, provided that no more than one member is phenyl; diphenylhydroxymethyl; diphenylhydroxymethyl wherein at least one of said phenyls is substituted with from one to three members each selected from the group consisting of loweralkyl, loweralkoxy, hydroxy, halo, and phenyl, provided that no more than one member is phenyl; and radicals of formulae:

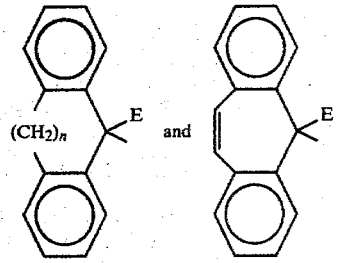

wherein n is 0, 1, or 2 and E is H or OH;

A taken individually is a member selected from the group consisting of hydrogen, acetyl, and phenyl, provided that when A is acetyl or phenyl, $R_1$ is a member selected from the group consisting of phenyl or phenyl substituted with from one to three members each selected from the group consisting of loweralkyl, loweralkoxy, hydroxy and halo;

$R_1$ and A taken together is a member selected from the group consisting of benzhydrylidene and radicals of formulae:

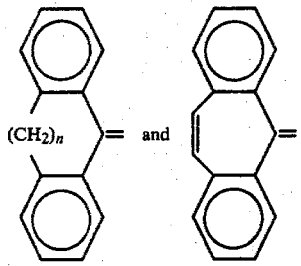

wherein n is 0, 1, or 2;

$R_1'$ taken individually is a member selected from the group consisting of hydrogen; methyl; diphenylmethyl; diphenylmethyl wherein at last one of the phenyl groups is substituted with from one to three members each selected from the group consisting of loweralkyl, loweralkoxy, hydroxy, halo, and phenyl, provided that no more than one member is phenyl; diphenylhydroxymethyl; diphenylhydroxymethyl wherein at least one of said phenyls is substituted with from one to three members each selected from the group consisting of loweralkyl, loweralkoxy, halo, hydroxy, and phenyl, provided that no more than one member is phenyl; and a radical of formula:

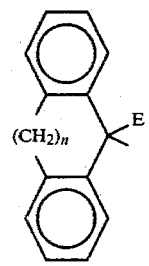

wherein n is 0, 1, or 2 and E is H or OH;

B taken individually is hydrogen;

$R_1'$ and B taken together is a member selected from the group consisting of benzhydrylidene and a radical of formula:

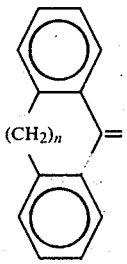

wherein n is 0, 1, or 2.

$R_1''$ taken individually is a member selected from the group consisting of hydrogen, diphenylmethyl;$ni-phenylmethyl wherein at least one of said phenyls is substituted with from one to three members each selected from the group consisting of loweralkyl, loweralkoxy, halo, hydroxy, and phenyl, provided that no more than one member is phenyl; diphenylhydroxymethyl; diphenylhydroxymethyl wherein at least one of said phenyls is substituted with from one to three members each selected from the group consisting of loweralkyl, loweralkoxy, hydroxy, halo, and phenyl, provided that no more than one member is phenyl; and radicals of formulae:

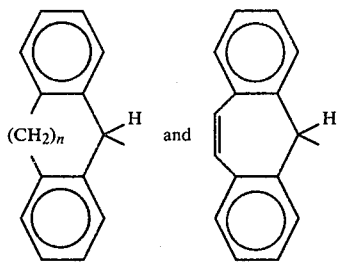

wherein n is 0, 1, or 2;

D taken individually is hydrogen;

$R_1''$ and D taken together is benzhydrylidene;

$R_2$ is a member selected from the group consisting of hydrogen and $C_1$–$C_4$ loweralkyl; and $R_3$ is a member selected from the group consisting of hydrogen; alkyl; cycloalkyl; phenylloweralkyl; phenylloweralkyl in which said phenyl is substituted with from one to three members each selected from the group consisting of loweralkyl, loweralkoxy, hydroxy, and halo; diphenyl($C_1$–$C_4$)-loweralkyl; diphenyl($C_1$–$C_4$)-loweralkyl in which at least one of said phenyls is substituted with from one to three members each selected from the group consisting of loweralkyl, loweralkoxy, hydroxy, halo, and phenyl, provided that no more than one member is phenyl; alkenyl; and alkynyl;

provided that at least one of said $R_1$, $R_1'$, and $R_1''$ is other than hydrogen and further provided that when $R_1''$ is other than hydrogen $R_1$, and $R_1'$, and A are each hydrogen; when $R_1'$ is hydrogen only one of $R_1$ and $R_1''$ is other than hydrogen; when $R_1'$ is methyl $R_1$ is other than hydrogen and $R_1''$ is hydrogen; and when $R_1'$ is other than hydrogen or methyl $R_1$, $R_1''$ and A are each hydrogen.

As used herein, loweralkyl and loweralkoxy may be straight or branched chain saturated aliphatic hydrocarbons having from one to eight carbon atoms, such as for example, methyl, ethyl, propyl, isopropyl, butyl, t-butyl, pentyl, and the like loweralkyls, and, respectively, the corresponding loweralkoxys, e.g., methoxy, ethoxy, propoxy, isopropoxy, butoxy, pentoxy, and the like. The term "$C_1$–$C_4$ loweralkyl" includes those loweralkyls having from one to four carbon atoms, such as for example, methyl, ethyl, n-propyl, isopropyl, n-butyl, isobutyl, sec-butyl, and the like. The terms "phenyl-($C_1$–$C_4$)loweralkyl" and "diphenyl($C_1$–$C_4$)loweralkyl" include only those compounds where the phenyl groups(s) are bonded to the terminal carbon atom of a straight chain loweralkyl, such as 2-phenethyl, 4-phenylbutyl, 4,4-diphenylbutyl, 3,3-diphenylpropyl, and the like. The term "1-phenyl-($C_7$–$C_9$)loweralkyl" includes groups having the following general formula:

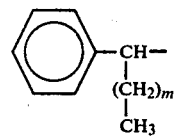

where M is 5, 6, or 7. The term "alkyl" includes straight or branched chain saturated aliphatic hydrocarbons having up to about sixteen carbon atoms, such as for example, the above mentioned lowerenoyls and further such radicals as hexyl, heptyl, octyl, nonyl, decyl, dodecyl, hexadecyl, and the like. The term "cycloalkyl" includes mono-, bi-, and tricyclic saturated and unsaturated aliphatic hydrocarbons having up to about ten carbon atoms, such as for example, cyclohexyl, adamantyl, 1-adamantyl-methyl, exo-norbornyl, endo-norbornyl, noradamantyl, anti-7-norbornenyl, and the like. The terms "alkenyl" and "alkynyl" include straight and branched chain hydrocarbons having from two to about eighteen carbon atoms and at least one double or triple bond respectively, such as for example, allyl, methallyl, 1-propargyl (1-propynyl), 2-pentenyl, and the like. The term "halo" includes fluoro, chloro, bromo and iodo.

Methods of Preparation

The compounds of Formula I may generally be prepared by reacting together: (a) an appropriately-substituted piperidine of Formula (II) with an appropriate activated amide (Formula III), or (b) an appropriate primary amine of Formula (VII) with an activated N-acyl piperidine of Formula (VI), said activation in either case having been achieved by treatment of the respective amide with a suitable activating agent selected from, for example, phosgene, $Me_3O^+BF_4^-$, $Et_3O^+BF_4^{31}$, $(MeO)_2SO_2$, $MeOSO_2F$, $POCl_3$, $PCl_5$ and the like.

Included in the terms "amide" and "N-acyl-piperidine" as used herein are the corresponding thio derivatives in which the carbonyl oxygen has been replaced by sulfur. In the case of the thio derivatives, there are additional suitable activating agents which may be employed, such as for example, loweralkyl halides (methyl halide being preferred), methyl tosylate, methyl sulfonic acid esters (e.g., methyl methanesulfonate) methyl trifluoromethylsulfonate, and the like.

The activated reactant of Formula (III) may be in either free base or acid addition salt form.

Specific preparative routes are given below:

(A) The compounds of Formula (I) may be prepared by reacting the appropriately-substituted piperidine of Formula (II) with an appropriate imidate ester of Formula (III). The methyl and ethyl esters are preferred. The substituted piperidine and the imidate ester (which may be present in either free base or acid addition salt form, the latter being shown) are stirred together in a suitable organic solvent such as, for example, a halocarbon (e.g., carbon tetrachloride, chloroform, 1,2-dichloroethane, and the like), a loweralkanol (e.g., methanol, ethanol, isopropanol, and the like), an aromatic hydrocarbon (e.g., benzene, xylene, toluene, and the like), dimethylsulfoxide, and the like. The temperature of the reaction is preferably from about 0° to about 25° C., and in some cases may be carried out as high as 50° C., but in any event the temperature of the reaction must not be high enough to decompose significant amounts of the imidate ester. The resulting product may be isolated and purified by techniques known in the art, e.g., by stripping off the solvent and recrystallizing the desired product in the free base or acid addition salt form. The above reaction scheme may be illustrated by the following, wherein A, B, D, $R_1$, $R_1'$, $R_1''$, $R_2$, and $R_3$ are as previously defined, Z is selected from the group consisting of loweralkoxy (preferably methoxy and ethoxy), loweralkyl-S— (preferably methylthio), chloro, and $Cl_2(O)PO—$, and X is a member selected from the group consisting of halide, $BF_4$, $FSO_3$, and $CH_3OSO_3$. Additionally, when Z is loweralkyl-S—, X may also be a member selected from the group consisting of (4-methylphenyl)$SO_3$, $CH_3SO_3$, and $CF_3SO_3$.

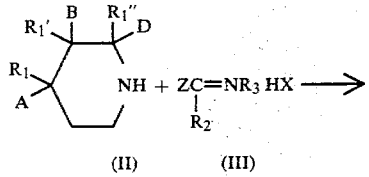

The compounds of Formula (I) wherein $R_2$ is hydrogen may also be prepared by an analogous route by substituting an appropriate compound of Formula (IIIA) or (IIIB) for the imidate ester of Formula (III). If the former is used, the resulting thiourea is then reduced (e.g., with Raney nickel) to give the desired compound. If the latter is used, silver chloride is employed as catalyst. These reaction schemes are illustrated by the following:

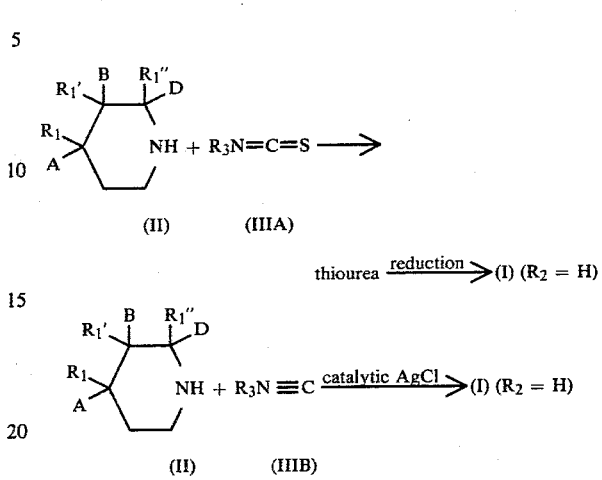

(B) The compounds of Formula (I) may also be prepared by reacting a suitably-substituted piperidine of Formula (II) with acetic formic anhydride or N,N-diloweralkylthioformamide (for $R_2=H$) or a $C_1$-$C_4$ loweralkyl anhydride (for $R_2=C_1$-$C_4$ loweralkyl), the anhydride preferably being present in excess. The piperidine and anhydride or thioformamide are combined with cooling and are allowed to stir for about 18 hours. The resulting reaction mixture, either dissolved in an organic solvent selected from the aforementioned halocarbon and aliphatic hydrocarbon solvents or without the addition of solvent, is then treated with an aqueous solution of a weak base (e.g., sodium bicarbonate) until the aqueous layer is neutral (for the anhydride route) or is washed with water (for the amide route). The organic layer is separated and any solvent present is removed to obtain the respective intermediate amides (IV), (IVA), and (V). The intermediate amide is treated either neat or in the presence of an organic solvent such as, for example, a halocarbon ($CHCl_3$, $CH_2Cl_2$) or a hydrocarbon (benzene, toluene) at 25° to 100° C. with a suitable activating agent, as described previously, for about two to three hours, to produce the activated derivative (VI), after which the reaction mixture is allowed to cool. Addition of the appropriate primary amine (VII) yields the desired product of Formula (I) which may be isolated and purified by known methods discussed above. The above reaction scheme may be illustrated by the following, wherein $R_1$, $R_1'$, $R_1''$, $R_2$, $R_3$, A, B, D, Z, and X are as originally defined:

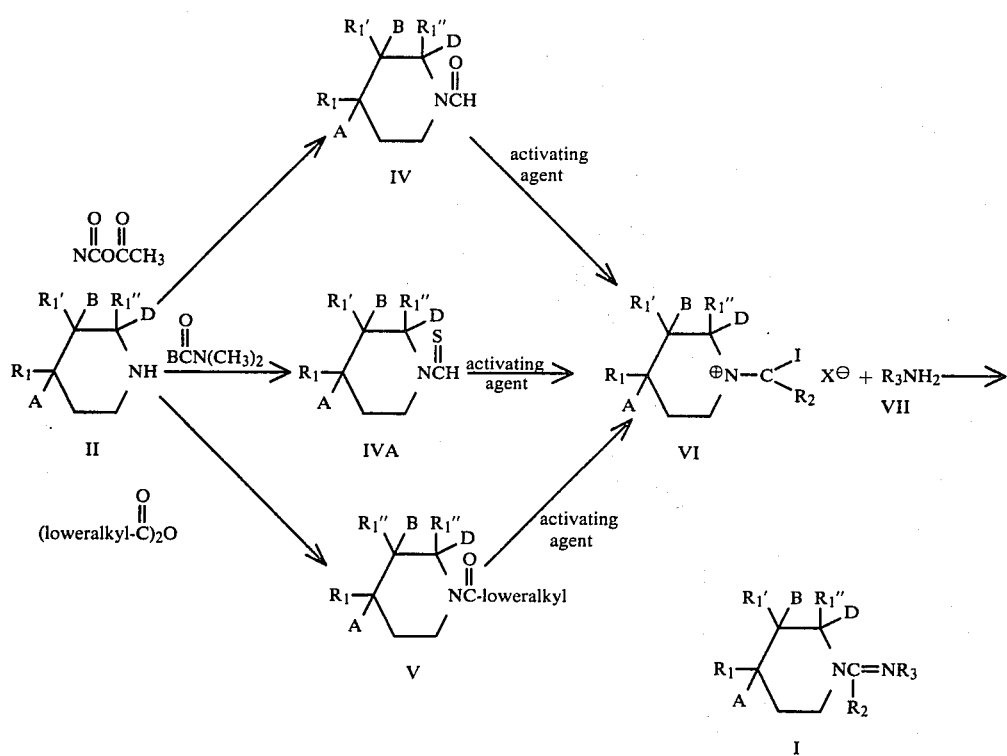

When Z is (loweralkyl)-S—, the compounds of Formula (I) wherein $R_2$=H may also be obtained by reacting is activated intermediate (VI) with the appropriate isocyanate of Formula (VIII), preferably at the reflux temperature of the solvent (e.g., toluene) for about nine days. This reaction scheme is illustrated by the following:

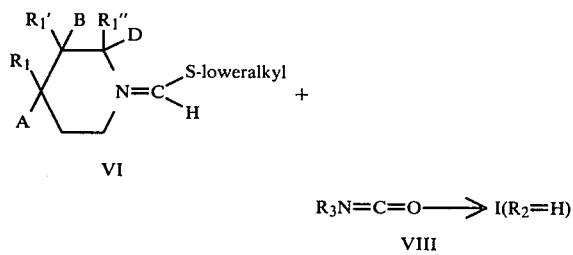

$$R_3N=C=O \longrightarrow I(R_2=H)$$
VIII

Because the subject compounds (I) possess a basic amidine group, they may be converted into the corresponding acid addition salts.

The acid addition salts may be prepared by reaction with an appropriate acid, as for example an inorganic acid such as a hydrohalic acid, i.e., hydrochloric, hydrobromic or hydriodic acid; sulfuric or nitric acid; phosphoric acid; an organic acid such as acetic, propionic, glycolic, pamoic, pyruvic, oxalic, malonic, succinic, maleic, picric, fumaric, malic, tartaric, citric, benzoic, cinnamic, mandelic, methanesulfonic, ethanesulfonic, benzenesulfonic, p-toluenesulfonic, salicylic, 2-naphthalenesulfonic or p-aminosalicylic acid. The therapeutically active, non-toxic acid addition salts of subject compounds (I) are included within the scope of the present invention.

The starting materials of Formulas (II), (III), (IV), (IVA), (V), (VI), (VII), and (VIII) are known or may be prepared by known methods. See generally R. C. Elderfield, *Heterocyclic Compounds*, Vol. 1, Ch. 9, pp 617–77 (1950). Preparative methods for compounds (II) are described in, for example, articles by F. Ravenna, Farmaco (Pavia) Ed. Sci., 14, 473–82 (1959) and E. Sury and K. Hoffman, Helv. Chim. Acta., 248, 2133 (1954). Preparative methods for compounds (III) and (IV) are described in, for example, articles by R. Ohme and E. Schmitz, Angew. Chem. Intern. Ed., 6, 566 (1967), F. Snydam, et al., J. Org. Chem., 34, 292 (1969), and K. Sechinger, Helv. Chim. Acta., 56, 776 (1973). Preparative methods for compounds (V) and (VI) are described in, for example, C. A. Buehler and D. E. Pearson, *Survey of Organic Syntheses*, Ch. 18, p 894 (1970).

Method of Testing

The compounds of the invention are useful for inhibition of gastric acid secretion as measured by the following test. Female Sprague-Dawley rats are fasted twenty-four hours before testing and are given water *ad libidum* while being kept in individual cages. On the day of testing, the rats are weighed and are selected so that the rats in each test weigh within a range of ± 20 grams.

Surgery is carried out under light ether anesthesia. As soon as the rat is anesthetized its teeth are removed and a mid-line incision is made on the abdomen about 1½ inches in length and the stomach and duodenum are exposed. If at this point the stomach is filled with food or fecal material, the rat is discarded. If the condition of the stomach is acceptable, a purse string stitch is placed on the fundic portion of the stomach with a suture, taking care not to pierce any blood vessels in the area. A small nick is then made into the stomach in the center of the purse string, and a cannula, consisting of a small vinyl tube with a flange on one end, is put into the stomach, and the purse string stitch is closed tightly around the flange. The test compound is administered either intraduodonally (i.d.) immediately after surgery or orally (p.o.) one hour prior to surgery at doses generally ranging from about 0.25 to about 160 mg/kg in a volume of 0.5 ml/100 grams rat. Control rats receive the test vehicle, 0.5% aqueous methyl cellulose.

After the surgery and (in the case of i.d. administration) after administration of the test compound, the abdominal wall and skin are closed simultaneously with three or four 18 mm wound clips and a collecting tube is placed on the cannula. Each rat is then placed in a box in which a longitudinal slit has been made to allow the cannula to hand freely and to allow the rat to move about unencumbered. After the rat has been allowed to stabilize for thirty minutes, the collection tube on the cannula is discarded and replaced with a clean tube to receive the gastric juice. Collections are made at one hour. At the end of the study, the cannula is removed and the rat is sacrificed.

The sample of gastric contents collected is drained into a centrifuge tube and centrifuged to pack down the sediment. The volume is read and a 1 ml aliquot of the supernatant is put into a beaker containing 10 ml distilled water and is titrated to pH7 using 0.01 N sodium hydroxide. Results are determined for Volume, Titratable Acid and Total Acid Output, where Volume equals total ml of gastric juice minus sediment; Titratable Acid (meg/l) equals amount of 0.01 N sodium hydroxide needed to titrate the acid to pH7; and Total Acid Output equals Titratable Acid times Volume. Results are reported as the $ED_{50}$ dose (mg/kg required to produce an average of 50% inhibition in Total Acid Output versus controls in all the animals tested for a particular compound) and as percent inhibition. The compounds of the invention all demonstrate a significant inhibition both i.d. and p.o. at less than 80 mg/kg, with preferred compounds having an $ED_{50}$ p.o. less than 20 mg/kg. In contrast, the prior art N-iminomethylpiperidine demonstrates no inhibition whatsoever at a dose of 100 mg/kg p.o. or at 80 mg/kg i.d.

It is well-known that excessive secretion of gastric hydrochloric acid leads to unneeded peptic activity and endangers the mucous lining of the stomach. The use of gastric antisecretory agents is thus desirable as an aid in the prevention and amelioration of distress occasioned by high concentrations of stomach acid.

DESCRIPTION OF THE PREFERRED EMBODIMENTS

Preferred compounds of the invention are those of Formula (I) wherein:

$R_1$ is a member selected from the group consisting of phenyl; phenyl substituted with from one to three members each selected from the group consisting of loweralkyl, loweralkoxy, halo, and phenyl, provided that no more than one member is phenyl; phenyl ($C_1$-$C_4$)loweralkyl; phenyl($C_1$-$C_4$)loweralkyl in which said phenyl is substituted with from one to three members each selected from the group consisting of loweralkyl, loweralkoxy and halo; diphenyl($C_1$-$C_4$)loweralkyl and diphenyl($C_1$-$C_4$) loweralkyl wherein at least one of said phenyls is substituted with from one to three members each selected from the group consisting of loweralkyl, loweralkoxy, halo, and phenyl, provided that no more than one member is phenyl;

$R_2$ is a member selected from the group consisting of hydrogen and methyl;

$R_3$ is a member selected from the group consisting of hydrogen; alkyl; cycloalkyl; phenylloweralkyl; phenylloweralkyl in which said phenyl is substituted with from one to three members each selected from the group consisting of loweralkyl, loweralkoxy, and halo; alkenyl, and alkynyl; and $R_1'$, $R_1''$, A, B, and D are each hydrogen.

More preferred compounds of the invention are those of Formula (I) wherein:

$R_1$ is a member selected from the group consisting of diphenylmethyl and diphenylmethyl wherein at least one of said phenyls is substituted with from one to three members each selected from the group consisting of loweralkyl, loweralkoxy, and halo;

$R_2$ is hydrogen;

$R_3$ is a member selected from the group consisting of hydrogen; alkyl; phenylloweralkyl; phenylloweralkyl in which said phenyl is substituted with from one to three members each selected from the group consisting of loweralkyl, loweralkoxy, and halo; alkenyl; and alkynyl; and $R_1'$, $R_1''$, A, B, and D are hydrogen.

Most preferred compounds of the invention are those of Formula (I) wherein $R_1$ is a member selected from the group consisting of diphenylmethyl and diphenylmethyl wherein one of said phenyls is substituted in the para-position with a member selected from the group consisting of loweralkyl, loweralkoxy, and halo; $R_2$ is a hydrogen; $R_3$ is a member selected from the group consisting of a hydrogen, straight chain alkyl, and phenylloweralkyl; and $R_1'$, $R_1''$, A, B, and D are all hydrogen.

DESCRIPTION OF THE METHOD OF TREATMENT AND PHARMACEUTICAL COMPOSITIONS

In view of the antisecretory activity of the subject compounds, there is further provided herein a method of inhibiting gastric acid secretion which comprises internally administering to a gastric hyperacidic subject (man or animal) an effective gastric acid secretion inhibiting amount of a substituted N-iminomethylpiperidine of Formula (I), in base of acid addition salt form, preferably in admixture with a pharmaceutically acceptable carrier. If an acid addition salt form is used, said salt must of course be pharmaceutically-acceptable and non-toxic. Pharmaceutical compositions comprising a subject compound (I) are also considered a further aspect of the present invention.

To prepare the pharmaceutical compositions of the present invention, a substituted N-iminomethylpiperidine of Formula (I) or an acid addition salt thereof is combined as the active ingredient in intimate admixture with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed, such as for example, water, glycols, oils, alcohols, flavoring agents, preservatives, coloring agents, and the like in the case of oral liquid preparations such as for example, suspensions, elixirs, and solutions; or carriers such as starches, sugars, diluents, granulating agents, lubricants, binders, disintegrating agents, and the like in a case of oral solid preparations, such as for example, powders, capsules, and tablets. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, although other ingredients, for example, to aid solubility or for preservative purposes, may be included. Injectable suspensions may also be prepared, in which case appropriate liquid carriers, suspending agents, and the like may be employed. The pharmaceutical compositions herein will contain, per dosage unit, e.g., tablet, capsule, powder, injection, teaspoonful, and the like, from about ten to about five hundred milligrams of the active ingredient, and preferably from about fifteen to about two hundred fifty milligrams.

The following examples are intended to illustrate but not to limit the scope of the present invention.

EXAMPLE I

4-Diphenylmethyl-1-iminomethylpiperidine hydrochloride hydrate

A suspension of 27.39 g (0.25 mole) of ethyl formimidate hydrochloride [prepared by the method of Ohme, et al., Angew. Chem. Intl. Ed., 6, 566(1967)] and 52.71 g (0.20 mole) of diphenyl-4-piperidylmethane in 80 ml of freshly-opened absolute ethanol was stirred magnetically under a calcium chloride tube overnight. The suspension was filtered and diethylether was added to the filtrate. The filtrate was stripped to dryness and the resulting oil was crystallized from isopropanol. The solid was then suspended in boiling ethyl acetate to obtain a higher melting form. Two recrystallizations from ethanol-ether yielded pure 4-diphenylmethyl-1-iminomethylpiperidine hydrochloride hydrate; m.p. 220°–221° C.

EXAMPLE II

Following the procedure of Example I, but substituting for the ethyl formimidate hydrochloride and diphenyl-4-piperidylmethane used therein, equivalent amounts of the appropriate starting materials, there are prepared the following:

| $R_1$ | Salt | A | $R_2$ | $R_3$ | m.p. (°C.) |
|---|---|---|---|---|---|
| diphenylmethyl- | HCl | H | $C_2H_5$ | H | 271.5–277.5 |
| (4-methoxyphenyl)benzyl | fumarate | H | H | H | 189.5–192.5 |
| α-(1,4-biphenyl)-α-hydroxybenzyl | HCl | H | H | H | 216–218 |
| phenyl | HCl | H | H | H | 204–205 |
| benzyl | HCl | H | H | H | 199–201.5 |
| phenyl | HCl | $\overset{O}{\underset{}{\|}}C-CH_3$ | H | H | 172–175 |
| α-(4-chlorophenyl)benzyl | fumarate | H | H | H | 192.5–194.5 |

EXAMPLE III

4-(Diphenylmethyl)-1-N-ethyliminomethyl-piperidine oxalate hemihydrate

A mixture of 8.00 g (0.029 mole) of N-formyl-4-diphenylmethylpiperidine and 3.61 g (2.67 ml, 0.029 mole) of dimethylsulfate was heated on a steam bath for two hours to give a clear thick syrup. To this material was then added 1.38 g (2.00 ml, 0.031 mole) of ethylamine in 15 ml of methylene chloride. The resulting solution was stirred for 1.5 hours at 25°, stripped, slurried in ether, and treated with 28 ml of 3 N sodium hydroxide solution. The ethereal layer was dried over potassium carbonate, filtered through diatomaceous earth filter aid and evaporated to give 8.77 g of yellow liquid. Treatment of this material in isopropanol with 3.26 g of oxalic acid dihydrate afforded 5.0 g of white solid m.p. 165°–175° C. Recrystallization from isopropanol afforded pure 4-(diphenylmethyl)-1-N-ethyliminomethylpiperidine oxalate hemihydrate as a white solid; m.p. 185°–187° C.

EXAMPLE IV

Following the procedure of Example III, but substituting for the N-formyl-4-diphenylmethylpiperidine and ethylamine used therein, equivalent amounts of the appropriate starting materials, there are prepared the following:

| $R_1$ | $R_2$ | $R_3$ | Salt | m.p. (°C.) |
|---|---|---|---|---|
| diphenylmethyl | H | —$CH_2CH=CH_2$ | cyclohexane sulfamate | 179.5–181 |
| " | H | i-propyl | fumarate | 175–178 |
| " | H | n-butyl | " | 193.5–195 |
| " | H | n-hexyl | " | 179–181.5 |
| " | H | n-heptyl | " | 175–178 |
| " | H | n-octyl | " | 157–159 |
| " | H | t-octyl | " | 227–229 |
| " | H | n-nonyl | " | 142–144.5 |
| " | H | n-decyl | succinate | 106–109 |
| " | H | n-dodecyl | fumarate hydrate | 143–145.5 |
| " | H | 1-adamantyl | fumarate | 275–276 |
| " | H | benzyl | cyclohexane sulfamate | 164.5–166.5 |
| " | H | phenethyl | cyclohexane sulfamate | 141–144 |

-continued $$R_1 \underset{R_2}{\overset{}{\diagdown}} \diagup NC=NR_3 \cdot \text{Salt}$$

| R₁ | R₂ | R₃ | Salt | m.p. (°C.) |
|---|---|---|---|---|
| " | H | p-chlorobenzyl | 2-naphthlene sulfonate | 222–224 |
| " | H | p-methoxybenzyl | 2-naphthalene sulfonate | 110.5–112.5 |
| α-(4-methoxyphenyl)benzyl | H | n-octyl | (E)-2-butenedioate | 154.5–156 |
| α-(4-methylphenyl)benzyl | H | n-octyl | (e)-2-butenedioate | 161–163.5 |
| diphenylmethyl | H | 4-methylbenzyl | perchlorate | 242–244 |
| " | H | phenyl | 4-toluenesulfonate | 285–286 |

EXAMPLE IVA

A mixture of 4-[(4-methoxyphenyl)phenylmethyl]-1-[(octylimino)methyl]piperidine (1,90 g. 0.0045 mole) and 42 ml of 47–49% hydrobromic acid was refluxed one hour, cooled, and the aqueous portion decanted from a thick oil. The oil was dissolved in methylene chloride, rendered neutral with aqueous sodium bicarbonate, dried and evaporated. The residue, 4-[(4-hydroxyphenyl)phenylmethyl]-1-[(octylimino)methyl]piperidine was converted to its naphthalenesulfonic acid salt, m.p. 177.5°–180° C.

EXAMPLE V 4-(Diphenylmethyl)-1-[(octylimino)methyl]piperidine Fumarate Hydrate A solution of triethyl oxonium fluoroborate [prepared from 104.6 g (0.737 mole) of boron trifluoride etherate and 56.04 g (47.37 ml, 0.606 mole) of epichlorohydrin] was dissolved in 800 ml of anhydrous methylene chloride and the resulting solution treated with 81.0 g (0.516 mole) of N-(n-octyl) formamide and stirred overnight at 25°. 4-Diphenylmethylpiperidine (130 g., 0.518 mole) was added and the mixture was stirred for four hours. A small amount of white solid was filtered off, the filtrate made basic with 3 N sodium hydroxide solution, separated, dried over potassium carbonate and evaporated to a yellow oil. This material was dissolved in isopropanol and treated with 60 g of fumaric acid with warming. Addition of an equal volume of acetone followed by ether caused a solid to form affording two crops of material m.p. 152°–157° C. These were combined and recrystallized from ethanol-water to give two crops of 4-(diphenylmethyl)-1-[(octylimino)methyl]piperidine fumarate hydrate; m.p. 157°–159° C.

EXAMPLE VI 4-(Diphenylmethyl)-1-piperidinecarbothioaldehyde

A solution of 20.0 g (0.08 mole) of 4-diphenylmethylpiperidine, 14.2 g (0.16 mole) of N,N-dimethylthioformamide and 50 ml of toluene was refluxed for 12 hours, cooled, and washed with water. The organic layer was separated, dried and stripped to an oil which was treated with diethyl ether to give a solid. Recrystallization of this material afforded a white crystalline solid, 4-(diphenylmethyl)-1-piperidinecarbothioaldehyde, m.p. 152°–154° C.

EXAMPLE VII

Following the above procedure, but substituting for 4-diphenylmethylpiperidine used therein, an equivalent amount of an appropriate piperidine, there are prepared the following:

$$R_1 \underset{A}{\overset{R_1'}{\diagdown}} \diagup \overset{S}{\underset{}{\|}} NCH$$

| R₁ | A | R₁' | m.p. (°C.) |
|---|---|---|---|
| 9-fluorenyl | H | H | 142–146 |
| H | H | Ph₂CH | 115–120 |
| benzylhydrylidene | | H | 131–134 |
| diphenylhydroxymethyl | H | H | 200–203 |

EXAMPLE VIII 4-(Diphenylmethyl)-1-N-(n-dodecyliminomethyl)-piperidine fumarate A solution of 5.54 g (0.019 mole) of 4-(diphenylmethyl)-1-piperidinecarbothioaldehyde in 20 ml of chloroform was treated with 2.65 g (1.16 ml, 0.019 mole) of methyl iodide and refluxed for one hour. The resulting solution was treated with 3.49 g (0.019 mole) of n-dodecylamine, refluxed one and one half hours, cooled, treated with aqueous sodium hydroxide and the organic layer separated. After drying, evaporation yielded an oil which was converted to the fumarate to yield 4-(diphenylmethyl)-1-N-(n-dodecyliminomethyl)piperidine fumarate; m.p. 143°–145.5° C.

EXAMPLE IX

Following the above procedure, but substituting for the 4-(diphenylmethyl)-1-piperidinecarbothioaldehyde and n-dodecylamine used therein, equivalent amounts of the appropriate starting materials, there are prepared the following:

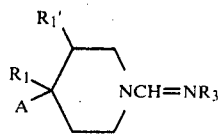

| $R_1$ | A | $R_1'$ | $R_3$ | Salt | m.p. (°C.) |
|---|---|---|---|---|---|
| diphenylmethyl | H | H | $\begin{array}{c}H \phantom{XX} H \\ \diagdown \phantom{X} \diagup \\ -(CH_2)_8C{=}C- \\ (CH_2)_7CH_3 \end{array}$ | fumarate hydrate | (sinter 125°) 131–135 |
| diphenylmethyl | H | H | $-CH_2C{\equiv}CH$ | HCl | 117–119 |
| 9H-fluoren-9-yl | H | H | n-$C_8H_{17}$ | HCl | 174–177 |
| H | H | diphenylmethyl | n-$C_8H_{17}$ | fumarate hydrate | (sinter 68.5°) 70–72 |
| -benzyhydrylidene- | | H | n-$C_8H_{17}$ | fumarate | 167–170 |
| diphenylhydroxymethyl | H | H | n-$C_8H_{17}$ | fumarate | (sinter 145°) 155–161 |
| H | | H | diphenylmethyl | H | fumarate | 185.5–187.5 |

EXAMPLE X

Alternate preparative routes illustrated for 4-(diphenylmethyl)-1-[(octylimino)methyl]piperidine (1) A mixture of 2.90 g (0.01 mole) of 4-(diphenylmethyl)-1-piperidinecarbothioaldehyde, 129 g (0.01 mole) of n-octylamine, 0.60 g (0.01 mole) of glacial acetic acid and 20 ml of toluene was heated with stirring at 60° for two days. The reaction mixture was made basic and concentrated to give an oil which was identified as 4-(diphenylmethyl)-1-[(octylimino)methyl]piperidine by vapor phase chromatography.

(2) A mixture of 2.0 g (0.0068 mole) of 4-(diphenylmethyl) -1-piperidinecarbothioaldehyde, 0.9 g (0.0069 mole) of n-octylamine, 2.16 g (0.010 mole) of mercuric oxide and 15 ml of isopropanol was refluxed overnight, filtered and concentrated. The residue was treated with fumaric acid to give 4-(diphenylmethyl)-1- [(octylimino)methyl]piperidine (E)-2-butenedioate (1:1) hydrate which was identified by comparison with an authentic sample by thin layer chromatography.

(3) A solution of 1.0 g (0.0034 mole) of 4-(diphenylmethyl) -1-piperidinecarbothioaldehyde, 0.59 g (0.0038 mole) of n-octyl isocyanate and 6 ml toluene were refluxed nine days. Vapor phase chromatography in conjunction with mass spectral analysis showed 4-(diphenylmethyl)-1-[(octylimino)methyl]piperidine in the amount of 17% in the reaction mixture.

(4) A solution of 1.0 g (0.0034 mole), of 4-(diphenylmethyl) -1-piperidinecarbothioaldehyde, 0.45 g (0.0034 mole) of n-octylamine, and 6.0 ml isopropanol was refluxed overnight. Vapor phase chromatography analysis of the reaction mixture showed 4-(diphenylmethyl)-1-[(octylimino)methyl]piperidine to be present.

(5) A solution of 6.0 g (0.035 mole) of n-octylisothiocyanate was dissolved in 25 ml of toluene, treated with 8.80 g (0.035 mole) of 4-diphenylmethylpiperidine and stirred at 25° for twelve hours. The mixture was cooled, filtered and evaporated. Chromatography of the residue through silica gel using chloroform as an eluent afforded a brown oil, 4-(diphenylmethyl)-N-octyl-1-piperidinecarbothioamide. A mixture of 1.0 g (0.0024 mole) of this material, 3 g of Raney Nickel and 15 ml of isopropanol was refluxed three hours, cooled, and filtered. Evaporation of the filtrate afforded an oil which was converted to a fumarate identified as 4-(diphenylmethyl)- 1-[(octylimino)methyl]piperidine (E)-2-butenedioate (1:1) hydrate by thin layer chromatography.

(6) A solution of N-formyl-4-diphenylmethylpiperidine 40.0 g (0.143 mole) and 50 ml of methylene chloride was treated with phosgene until gas evolution ceased. After refluxing for one hour, the excess phosgene was removed under reduced pressure, the reaction was diluted with 50 ml of methylene chloride and 24.8 ml (0.145 mole) of n-octyl amine in 25 ml of methylene chloride was introduced at such a rate as to maintain mild reflux. Triethyl amine (28 ml) was added slowly, the reaction stirred for ten minutes, and then poured into water. The organic phase was separated, washed with 20% sodium hydroxide solution, dried, and stripped to an oil which was converted to 4-(diphenylmethyl)-1-[(octylimino)methyl]piperidine (E)-2-butenedioate (1:1) hydrate, identified by thin layer chromatography.

(7) A mixture of 5.60 g (0.022 mole) of 4-dibenylmethylpiperidine, 3.50 g (0.022 mole) of n-octylisonitrile, 0.26 g (0.002 mole) of silver chloride, and 10 ml of toluene was stirred 48 hours at 25°, filtered, stripped, and the residue dissolved in methylene chloride. Extraction with 10% sodium hydroxide, drying and filtration of the organic layer followed by evaporation afforded 4-(diphenylmethyl)-1-[(octylimino)methyl]-piperidine isolated as the fumarate salt, which was identified by thin layer chromatography.

EXAMPLE XI

Following the test procedure previously described, the following compounds were tested for their antisecretory activity. The $ED_{50}$ values for p.o. administration and the percent inhibition for i.d. administration at 20 mg/kg are tabulated below ($R_1'$=H except where noted):

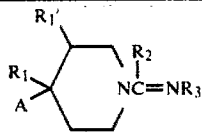

| $R_1$ | A | $R_2$ | $R_3$ | $ED_{50}$ (mg/kg po) | Percent Inhibition at 20 mg/kg id |
|---|---|---|---|---|---|
| diphenylmethyl | H | H | H | 0.7 | 100 |
| " | " | " | ethyl | 4.3 | 100 |
| " | " | " | —CH$_2$CH=CH$_2$ | 10.2 | 100 |
| " | " | " | —CH$_2$C≡CH | 6.07 | 100 |
| " | " | " | i-propyl | 9.8 | 96 |
| " | " | " | n-butyl | 8.6 | 100 |
| " | " | " | n-hexyl | 8.7 | 96 |
| " | " | " | n-heptyl | 11.6 | 72 |
| " | " | " | n-octyl | 9.8 | 64 |
| " | " | " | t-octyl | 35 | 28* |
| " | " | " | n-nonyl | 19.6 | 93 |
| " | " | " | n-decyl | 8.2 | 79 |
| " | " | " | n-dodecyl | 53 | 80 |
| " | " | " | 1-adamantyl | 37.0 | 0** |
| " | " | " | —(CH$_2$)$_8$CH=CH(CH$_2$)$_7$CH$_3$ | 66 | 78.9 |
| " | " | " | benzyl | 3.3 | 100 |
| " | " | " | phenethyl | 3.7 | 100 |
| " | " | " | p-chlorobenzyl | 20.7 | 94 |
| " | " | ethyl | H | >40 | 75 |
| " | " | H | p-methoxybenzyl | <40 | 63 |
| α-(p-methoxyphenyl)benzyl | " | " | H | 12.1 | 100 |
| " | " | " | n-octyl | 16.9 | 62 |
| α-(4-chlorophenyl)benzyl | " | " | H | 2.32 | 100 |
| α-(1,4-biphenyl)-α-hydroxybenzyl | " | " | H | >80 | 72 |
| phenyl | " | " | H | Ca 40 | 77 |
| 9-fluorenyl | " | " | n-octyl | 15.9 | 48 |
| benzyl | " | " | H | 114 | 98 |
| α-(4-methylphenyl)benzyl | " | " | n-octyl | — | 73 |
| diphenylmethyl | " | methyl | n-octyl | 14 | 98 |
| " | " | H | —(CH$_2$)$_4$—C$_6$H$_5$ | 8.1 | 82 |
| phenyl | O‖—CCH$_3$ | " | H | — | 71 |
| benzhydrylidene | " | " | n-octyl | 0.625 | 68.2 |
| H | H | " | n-octyl | 18.3 | 92.2 † |
| H | " | " | H | 7 †† | 68 † |
| α-(4-hydroxyphenyl)benzyl | " | " | n-octyl | 2 †† | — |
| α-(phenyl)-α-hydroxybenzyl | " | " | " | 5 †† | — |
| H | " | " | H | Inactive at 80 | 0*** |

*98% inhibition at 80 mg/kg i.d.
**52% inhibition at 80 mg/kg i.d
***Prior art compound
† $R_1'$ diphenylmethyl
†† compound administered intraperitoneally

EXAMPLE XII

Following the procedure described by Buehler and Pearson [Survey of Organic Syntheses, Ch. 18, p 894 (1970)] and using the appropriate substituted piperidine and anhydride, there are prepared the following piperidine amides, wherein the following substituents are in the two ($R_1''$), three ($R_1'$) or four ($R_1$) position:

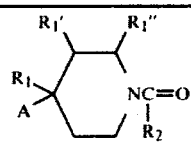

| Substituent | Position of Substituent | $R_2$ | A |
|---|---|---|---|
| diphenylmethyl | 4 | H | H |
| α-(4-chlorophenyl)benzyl | 4 | H | H |
| α-(4-methylphenyl)benzyl | 4 | H | H |
| α-(4-methoxyphenyl)benzyl | 4 | H | H |
| α-(4-chlorophenyl)benzyl | 3 | H | H |
| 9-fluorenyl | 3 | H | H |
| diphenylmethyl | 3 | H | H |
| phenyl | 4 | H | H |
| phenyl | 4 | H | phenyl |
| 4-chlorophenyl | 4 | H | H |

-continued

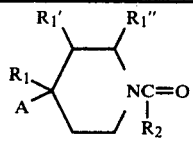

| Substituent | Position of Substituent | R2 | A |
|---|---|---|---|
| 4-chlorophenyl | 4 | H | phenyl |
| 4-methoxyphenyl | 4 | H | H |
| 4-methoxyphenyl | 4 | H | phenyl |
| 4-chlorobenzyl | 4 | H | H |
| phenyl | 4 | methyl | phenyl |
| phenyl | 4 | n-butyl | phenyl |
| α-(1,4-biphenyl)benzyl | 4 | H | H |
| α-(1,4-biphenyl)benzyl | 4 | methyl | H |
| α-(1,4-biphenyl)benzyl | 4 | n-butyl | H |
| 2,2-diphenylethyl | 4 | H | H |
| 2,2-diphenylethyl | 4 | methyl | H |
| 2,2-diphenylethyl | 4 | n-butyl | H |
| 10,11-dihydro-5H-dibenzo[a,d]cycloheptene-5-yl | 2 | H | H |
| 10,11-dihydro-5H-dibenzo[a,d]cycloheptene-5-yl | 2 | methyl | H |
| 10,11-dihydro-5H-dibenzo[a,d]cycloheptene-5-yl | 2 | n-butyl | H |
| 10,11-dihydro-5H-dibenzo[a,d]cycloheptene-5-yl | 4 | H | H |
| 10,11-dihydro-5H-dibenzo[a,d]cycloheptene-5-yl | 4 | methyl | H |
| 10,11-dihydro-5H-dibenzo[a,d]cycloheptene-5-yl | 4 | n-butyl | H |
| 4,4-diphenyl-n-butyl | 4 | H | H |
| 4,4-diphenyl-n-butyl | 4 | methyl | H |
| 4,4-diphenyl-n-butyl | 4 | n-butyl | H |
| 4-methoxybenzyl | 4 | H | H |
| benzyl | 4 | H | H |
| 9-fluorenyl | 4 | H | H |
| diphenylmethyl | 4 | methyl | H |
| diphenylmethylene | 4 | methyl | H |
| α-(4-chlorophenyl)benzyl | 4 | methyl | H |
| α-(4-methylphenyl)benzyl | 4 | methyl | H |
| α-(4-methoxyphenyl)benzyl | 4 | methyl | H |
| diphenylmethyl | 3 | methyl | H |
| 9-fluorenyl | 3 | methyl | H |
| α-(4-chlorophenyl)benzyl | 3 | methyl | H |
| phenyl | 4 | methyl | H |
| 9-fluorenyl | 4 | methyl | H |
| 4-chlorophenyl | 4 | methyl | H |
| 4-methoxyphenyl | 4 | methyl | H |
| 4-chlorobenzyl | 4 | methyl | H |
| 4-methoxybenzyl | 4 | methyl | H |
| benzyl | 4 | methyl | H |
| diphenylmethyl | 4 | n-butyl | H |
| diphenylmethylene | 4 | n-butyl | H |
| α-(4-chlorophenyl)benzyl | 4 | n-butyl | H |
| α-(4-methoxyphenyl)benzyl | 4 | n-butyl | H |
| α-(4-methylphenyl)benzyl | 4 | n-butyl | H |
| diphenylmethyl | 3 | n-butyl | H |
| 9-fluorenyl | 3 | n-butyl | H |
| 9-fluorenyl | 4 | n-butyl | H |
| α-(4-chlorophenyl)benzyl | 3 | n-butyl | H |
| 5H-dibenzo[a,d]cyclohepten-5-yl | 2 | H | H |
| 5H-dibenzo[a,d]cyclohepten-5-yl | 2 | methyl | H |
| 5H-dibenzo[a,d]cyclohepten-5-yl | 2 | n-butyl | H |
| 10,11-dihydro[a,d]cyclohepten-5-yl | 2 | H | H |
| 10,11-dihydro[a,d]cyclohepten-5-yl | 2 | methyl | H |
| 10,11-dihydro[a,d]cyclohepten-5-yl | 2 | n-butyl | H |
| phenyl(octyl)methyl | 4 | H | H |
| phenyl(octyl)methyl | 4 | methyl | H |
| phenyl(octyl)methyl | 4 | n-butyl | H |
| phenyl(hexyl)methyl | 4 | H | H |
| phenyl(hexyl)methyl | 4 | methyl | H |
| phenyl(hexyl)methyl | 4 | n-butyl | H |
| phenyl | 4 | n-butyl | H |
| 4-chlorophenyl | 4 | n-butyl | H |
| 4-methoxyphenyl | 4 | n-butyl | H |
| benzyl | 4 | n-butyl | H |
| 4-chlorobenzyl | 4 | n-butyl | H |
| 4-methoxybenzyl | 4 | n-butyl | H |

-continued

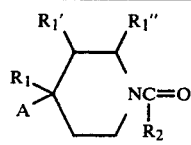

| Substituent | Position of Substituent | R2 | A |
|---|---|---|---|
| diphenylmethyl | 2 | H | H |
| diphenylmethyl | 2 | methyl | H |
| diphenylmethyl | 2 | n-butyl | H |
| 5H-dibenzo[a,d]cyclohepten-5-yl | 4 | H | H |
| 5H-dibenzo[a,d]cyclohepten-5-yl | 4 | methyl | H |
| 5H-dibenzo[a,d]cyclohepten-5-yl | 4 | n-butyl | H |

EXAMPLE XIII

Following the procedure described by Buehler and Pearson [Survey of Organic Syntheses, Ch. 18, p 894 (1970)] and using the appropriate substituted piperidine and anhydride, there are prepared the following piperidine amides:

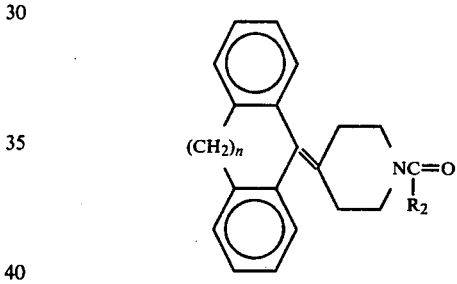

| Position of Substituent | n | R2 |
|---|---|---|
| 4 | 0 | H |
| 4 | 0 | CH3 |
| 4 | 0 | n-butyl |
| 4 | 1 | H |
| 4 | 1 | CH3 |
| 4 | 1 | n-butyl |
| 4 | 2 | H |
| 4 | 2 | CH3 |
| 4 | 2 | n-butyl |
| 3 | 0 | H |
| 3 | 0 | CH3 |
| 3 | 0 | n-butyl |
| 3 | 1 | H |
| 3 | 1 | CH3 |
| 3 | 1 | n-butyl |
| 3 | 2 | H |
| 3 | 2 | CH3 |
| 3 | 2 | n-butyl |

EXAMPLE XIV

Following the procedure of Example XIII, there are prepared the following piperidine amides:

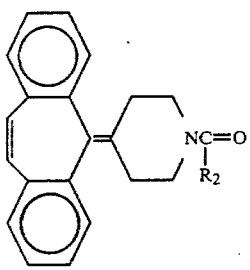

wherein R$_2$=hydrogen, methyl, or n-butyl.

EXAMPLE XV

Following the procedure of Example XIII, there are prepared the following piperidine amides:

| Position of Substituent | R$_2$ |
|---|---|
| 4 | H |
| " | CH$_3$ |
| " | n-butyl |
| 3 | H |
| " | CH$_3$ |
| " | n-butyl |
| 2 | H |
| " | CH$_3$ |
| " | n-butyl |

EXAMPLE XVI

Following procedures described in the references given above for compounds of Formula (III), the following are prepared:

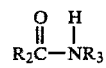

| R$_2$ | R$_3$ |
|---|---|
| H | —(CH$_2$)$_{11}$CH$_3$ |
| H | —(CH$_2$)$_7$CH$_3$ |
| H | —(CH$_2$)$_{14}$CH$_3$ |
| H | —(CH$_2$)$_4$CH=CHCH$_2$CH$_3$ |
| H | cis-(CH$_2$)$_5$CH=CH(CH$_2$)$_{10}$CH$_3$ |
| H | —(CH$_2$)$_6$C≡CH |
| H | 4-ClPh— |
| H | 4-MeOPh— |
| H | 4-MePh— |
| H | —CH$_2$C≡CH |
| H | exo-2-norbornyl |
| H | endo-2-norbornyl |
| H | 1-decahydronaphthyl |
| H | 1-adamantyl |
| H | 2-bicyclo[2.2.2]octyl |
| H | anti-7-norbornenyl |
| H | endo-bicyclo[3.2.1]octyl |
| H | 1-adamantylmethyl |
| Me | H |
| Me | —C$_2$H$_5$ |
| Me | —(CH$_2$)$_5$CH$_3$ |
| Me | —(CH$_2$)$_7$CH$_3$ |

-continued

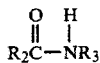

| R$_2$ | R$_3$ |
|---|---|
| Me | —(CH$_2$)$_{14}$CH$_3$ |
| Me | —(CH$_2$)$_4$CH=CHCH$_2$CH$_3$ |
| Me | cis-(CH$_2$)$_5$CH=CH(CH$_2$)$_{10}$CH$_3$ |
| Me | —CH$_2$C≡CH |
| Me | (CH$_2$)$_6$C≡CH |
| Me | Ph |
| Me | 4-ClPh— |
| Me | 4-MeOPh— |
| Me | 4-MePh— |
| Me | PhCH$_2$— |
| Me | 4-ClPhCH$_2$— |
| Me | 4-MePhCH$_2$— |
| Me | 4-MeOPhCH$_2$ |
| Me | PhCH$_2$CH$_2$— |
| Me | exo-2-norbornyl |
| Me | endo-2-norbornyl |
| Me | 1-decahydronaphthyl |
| Me | 1-adamantyl |
| Me | 2-bicyclo[2.2.2]octyl |
| Me | anti-7-norbornenyl |
| Me | endo-bicyclo[3.2.1]octyl |
| Me | 1-adamantylmethyl |
| n-Butyl ("Bu") | H |
| Bu | C$_2$H$_5$ |
| Bu | —CH$_2$CH=CH$_2$ |
| Bu | (CH$_2$)$_7$CH$_3$ |
| Bu | (CH$_2$)$_{14}$CH$_3$ |
| Bu | —(CH$_2$)$_4$CH=CHC$_2$H$_5$ |
| Bu | cis-(CH$_2$)$_5$CH=CH(CH$_2$)$_{10}$CH$_3$ |
| Bu | —CH$_2$C≡CH |
| Bu | (CH$_2$)$_6$C≡H |
| Bu | 4-ClPh |
| Bu | 4-MeOPh |
| Bu | 4-MePh |
| Bu | Ph |
| Bu | PhCH$_2$ |
| Bu | 4-ClPhCH$_2$— |
| Bu | 4-MePhCH$_2$— |
| Bu | 4-MeOPhCH$_2$— |
| Bu | PhCH$_2$CH$_2$ |
| Bu | exo-2-norbornyl |
| Bu | endo-2-norbornyl |
| Bu | 1-decahydronaphthyl |
| Bu | 1-adamantyl |
| Bu | 2-bicyclo[2.2.2]octyl |
| Bu | anti-7-norbornenyl |
| Bu | endo-bicyclo[3.2.1]octyl |
| Bu | 1-adamantylmethyl |
| H | diphenylmethyl |
| Me | diphenylmethyl |
| Bu | diphenylmethyl |
| H | 3,3-diphenyl-n-propyl |
| Me | 3,3-diphenyl-n-propyl |
| Bu | 3,3-diphenyl-n-propyl |

EXAMPLE XVII

Following the procedure of either Example I or Example III, but substituting for the ethyl formimidate hydrochloride and diphenyl-4-piperidylmethane or N-formyl- 4-diphenylmethylpiperidine and ethylamine, respectively, used therein, equivalent amounts of the appropriate starting materials such as described in Examples XII and XVI, there are prepared the following, wherein the following substituents are in the two (R$_1$"), three (R$_1$'), or four (R$_1$) positions:

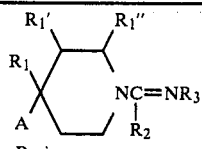

| Substituent ($R_1$, $R_1'$, $R_1''$) | Position of Substituent | $R_2$ | $R_3$ | A |
|---|---|---|---|---|
| diphenylmethyl | 2 | H | H | H |
| diphenylmethyl | 3 | " | " | " |
| 9-fluorenyl | " | " | " | " |
| α-(4-chlorophenyl)benzyl | " | " | " | " |
| diphenylhydroxymethyl | 4 | " | " | " |
| 10,11-dihydro-5H-dibenzo[a,d]cyclohepten-5-yl | " | " | " | " |
| 4-chlorobenzyl | " | " | " | " |
| 4-methoxyphenyl | " | " | " | " |
| diphenylmethyl | " | " | $-(CH_2)_{11}CH_3$ | " |
| 4-chlorophenyl | " | " | " | " |
| α-(4-methylphenyl)benzyl | " | " | " | " |
| 4-chlorobenzyl | " | " | " | " |
| α-(4-chlorophenyl)-α-hydroxybenzyl | " | " | " | " |
| α-(4-chlorophenyl)benzyl | 3 | " | " | " |
| 9-fluorenyl | " | " | " | " |
| 4-methoxybenzyl | 4 | " | $-(CH_2)_7CH_3$ | " |
| 9-fluorenyl | 3 | " | " | " |
| diphenylhydroxymethyl | 2 | " | " | " |
| α-(4-chlorophenyl)benzyl | 3 | " | " | " |
| diphenylhydroxymethyl | 4 | " | " | " |
| 5H-dibenzo[a,d]cyclohepten-5-yl | " | " | " | " |
| phenyl | " | " | " | phenyl |
| diphenylmethyl | " | " | $-(CH_2)_{14}CH_3$ | H |
| α-(4-chlorophenyl)-α-hydroxybenzyl | " | " | " | " |
| α-(4-chlorophenyl)benzyl | 3 | " | " | " |
| 9-fluorenyl | 4 | " | " | " |
| α-(4-methylphenyl)benzyl | " | " | " | " |
| 4-chlorophenyl | " | " | " | " |
| 4-methoxybenzyl | " | " | " | " |
| diphenylmethyl | " | " | $-(CH_2)_4CH=CHCH_2CH_3$ | " |
| α-(4-methoxyphennyl)benzyl | " | " | " | " |
| diphenylmethyl | 3 | " | " | " |
| 10,11-dihydro-5-hydroxy-5H-dibenzo[a,d]cyclohepten-5-yl | " | " | " | " |
| 9-fluorenyl | " | " | " | " |
| diphenylhydroxymethyl | 4 | " | " | " |
| phenyl | " | " | " | " |
| 4-chlorobenzyl | " | " | " | " |
| diphenylmethyl | " | " | cis-$(CH_2)_5CH=CH(CH_2)_{10}CH_3$ | " |
| α-(4-chlorophenyl)benzyl | 3 | " | " | " |
| 9-hydroxy-9-fluorenyl | 4 | " | " | " |
| α-(4-chlorophenyl)-α-hydroxybenzyl | " | " | " | " |
| 4-methoxyphenyl | " | " | " | " |
| benzyl | " | " | " | " |
| α-(4-methylphenyl)benzyl | " | " | " | " |
| diphenylmethyl | " | " | $(CH_2)_6C\equiv CH$ | " |
| α-(4-chlorophenyl)benzyl | " | " | " | " |
| α-(4-methoxyphenyl)-α-hydroxybenzyl | " | " | " | " |
| 9-fluorenyl | 3 | " | " | " |
| α-(4-chlorophenyl)benzyl | " | " | " | " |
| diphenylmethyl | 2 | " | " | " |
| phenyl | 4 | " | " | " |
| 4-methoxybenzyl | " | " | " | " |
| diphenylmethyl | " | " | $-CH_2CH\equiv CH$ | " |
| α-(4-methoxyphenyl)benzyl | " | " | " | " |
| α-(4-methylphenyl)benzyl | " | " | " | " |
| hydroxybenzyl | " | " | " | " |
| α-(4-chlorophenyl)benzyl | 3 | " | " | " |
| 9-fluorenyl | 4 | " | " | " |
| 10,11-dihydro-5H-dibenzo[a,d]cyclohepten-5-yl | " | " | " | " |
| 4-methoxyphenyl | " | " | " | phenyl |
| 4-chlorobenzyl | " | " | " | H |
| diphenylmethyl | " | " | exo-2-norbornyl | " |

-continued

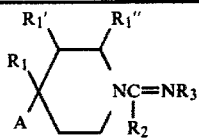

| Substituent (R₁, R₁', R₁") | Position of Substituent | R₂ | R₃ | A |
|---|---|---|---|---|
| α-(4-methylphenyl)benzyl | " | " | " | " |
| α-(4-methoxyphenyl)-α-hydroxybenzyl | " | " | " | " |
| diphenylmethyl | 3 | " | " | " |
| 9-fluorenyl | " | " | " | " |
| phenyl | 4 | " | " | " |
| 4-chlorobenzyl | " | " | " | " |
| α-(4-chlorophenyl)benzyl | " | " | endo-2-norbornyl | " |
| diphenylmethyl | " | " | " | " |
| diphenylhydroxymethyl | " | " | " | " |
| α-(4-chlorophenyl)benzyl | 3 | " | " | " |
| 9-fluorenyl | " | " | " | " |
| 4-methylphenyl | 4 | " | " | " |
| benzyl | " | " | " | " |
| diphenylmethyl | " | " | 1-decahydronaphthyl | " |
| α-(4-methoxyphenyl)benzyl | " | " | " | " |
| α-(4-methylphenyl)-α-hydroxybenzyl | " | " | " | " |
| diphenylmethyl | 3 | " | " | " |
| 9-fluorenyl | " | " | " | " |
| phenyl | 4 | " | " | " |
| 4-chlorobenzyl | " | " | " | " |
| α-(4-methoxyphenyl)benzyl | " | " | 1-adamantyl | " |
| 10,11-dihydro-5-hydroxy-5H-dibenzo[a,d]cyclohepten-5-yl | " | " | " | " |
| α(4-chlorophenyl)-α-hydroxybenzyl | " | " | " | " |
| α(4-chlorophenyl)benzyl | 3 | " | " | " |
| 9-fluorenyl | " | " | " | " |
| 4-chlorophenyl | 4 | " | " | phenyl |
| benzyl | " | " | " | H |
| diphenylmethyl | " | " | 2-bicyclo[2.2.2]octyl | H |
| α-(4-methoxyphenyl)benzyl | " | " | " | " |
| diphenylhydroxymethyl | " | " | " | " |
| diphenylmethyl | 3 | " | " | " |
| 9-fluorenyl | " | " | " | " |
| phenyl | " | " | " | " |
| 4-methoxybenzyl | " | " | " | " |
| diphenylmethyl | " | " | anti-7-norbornenyl | " |
| α-(4-chlorophenyl)benzyl | " | " | " | " |
| α-(4-methylphenyl)-α-hydroxybenzyl | " | " | " | " |
| diphenylmethyl | 3 | " | " | " |
| 9-fluorenyl | " | " | " | " |
| phenyl | 4 | " | " | " |
| 4-chlorobenzyl | " | " | " | " |
| diphenylmethyl | " | " | endo-bicyclo[3.2.1]octyl | " |
| α-(4-methylphenyl)benzyl | " | " | " | " |
| diphenylhydroxymethyl | " | " | " | " |
| α-(4-chlorophenyl)benzyl | 3 | " | " | " |
| 9-fluorenyl | " | " | " | " |
| diphenylhydroxymethyl | 2 | " | " | " |
| 4-methoxyphenyl | 4 | " | " | " |
| benzyl | " | " | " | " |
| diphenylmethyl | " | " | 1-adamantylmethyl | " |
| α-(4-methoxyphenyl)benzyl | " | " | " | " |
| α-(4-chlorophenyl)-α-hydroxybenzyl | " | " | " | " |
| α-(4-chlorophenyl)benzyl | 3 | " | " | " |
| 9-fluorenyl | " | " | " | " |
| phenyl | 4 | " | " | " |
| 4-methoxybenzyl | " | " | " | " |
| diphenylmethyl | " | methyl | H | " |
| α-(4-methoxyphenyl)benzyl | " | " | " | " |
| α-(4-chlorophenyl)-α-hydroxybenzyl | " | " | " | " |
| 5-hydroxy-5H-dibenzo[a,d]cyclohepten-5-yl | " | " | " | " |
| α-(4-chlorophenyl)benzyl | 3 | " | " | " |
| 9-fluorenyl | " | " | " | " |
| diphenylmethyl | 2 | " | " | " |

-continued

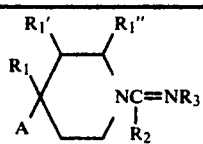

| Substituent (R$_1$, R$_1'$, R$_1''$) | Position of Substituent | R$_2$ | R$_3$ | A |
|---|---|---|---|---|
| 4-chlorophenyl | 4 | " | " | " |
| benzyl | " | " | " | " |
| diphenylmethyl | " | " | —C$_2$H$_5$ | " |
| α-(4-methoxyphenyl)benzyl | " | " | " | " |
| α-(methylphenyl)benzyl hydroxybenzyl | " | " | " | " |
| diphenylmethyl | 3 | " | " | " |
| 9-hydroxy-9-fluorenyl | 4 | " | " | " |
| 4-methoxyphenyl | " | " | " | " |
| 10,11-dihydro-5H-dibenzo[a,d]cyclohepten-5-yl | " | " | " | " |
| benzyl | " | " | " | " |
| α-(4-methylphenyl)benzyl | " | " | —(CH$_2$)$_7$CH$_3$ | " |
| diphenylhydroxymethyl | " | " | " | " |
| α-(4-chlorophenyl)benzyl | 3 | " | " | " |
| 9-fluorenyl | " | " | " | " |
| phenyl | 4 | " | " | " |
| benzyl | " | " | " | " |
| diphenylmethyl | " | " | —(CH$_2$)$_{14}$CH$_3$ | " |
| α-(4-chlorophenyl)benzyl | " | " | " | " |
| α-(4-methoxyphenyl)-α-hydroxybenzyl | " | " | " | " |
| diphenylmethyl | 3 | " | " | " |
| 9-fluorenyl | " | " | " | " |
| 4-methoxyphenyl | 4 | " | " | " |
| 4-chlorobenzyl | " | " | " | " |
| diphenylmethyl | " | " | —CH$_2$CH=CH$_2$ | " |
| α-(4-methoxyphenyl)benzyl | " | " | " | " |
| phenyl | " | " | " | phenyl |
| diphenylhydroxymethyl | " | " | " | H |
| α-(4-chlorophenyl)benzyl | 3 | " | " | " |
| 9-fluorenyl | " | " | " | " |
| 4-chlorophenyl | 4 | " | " | " |
| benzyl | " | " | " | " |
| diphenylmethyl | " | " | —(CH$_2$)$_4$CH=CHCH$_2$CH$_3$ | " |
| α-(4-methylphenyl)benzyl | " | " | " | " |
| α-(4-chlorophenyl)-α-hydroxybenzyl | " | " | " | " |
| diphenylmethyl | 3 | " | " | " |
| 9-fluorenyl | " | " | " | " |
| phenyl | 4 | " | " | " |
| 4-chlorobenzyl | " | " | " | " |
| diphenylmethyl | " | " | cis-(CH$_2$)$_5$CH=CH(CH$_2$)$_{10}$CH$_3$ | " |
| α-(4-methoxyphenyl)benzyl | " | " | " | " |
| diphenylhydroxymethyl | " | " | " | " |
| 9-fluorenyl | 3 | " | " | " |
| α-(4-chlorophenyl)benzyl | " | " | " | " |
| 4-methoxyphenyl | 4 | " | " | " |
| benzyl | " | " | " | " |
| diphenylmethyl | " | " | —CH$_2$C≡CH | " |
| α-(4-methylphenyl)benzyl | " | " | " | " |
| α-(4-chlorophenyl-α-hydroxybenzyl | " | " | " | " |
| diphenylmethyl | 3 | " | " | " |
| 9-hydroxy-9-fluorenyl | 4 | " | " | " |
| phenyl | " | " | " | " |
| 4-methoxybenzyl | " | " | " | " |
| diphenylmethyl | " | " | —(CH$_2$)$_6$C≡CH | " |
| α-(4-chlorophenyl)benzyl | " | " | " | " |
| diphenylhydroxymethyl | " | " | " | " |
| diphenylmethyl | 3 | " | " | " |
| 9-fluorenyl | " | " | " | " |
| diphenylhydroxymethyl | 2 | " | " | " |
| 4-chlorophenyl | 4 | " | " | " |
| 4-chlorobenzyl | " | " | " | " |
| diphenylmethyl | " | " | benzyl | " |
| α-(4-chlorophenyl)benzyl | " | " | 4-chlorobenzyl | " |
| diphenylhydroxymethyl | " | " | 4-methoxybenzyl | " |
| diphenylmethyl | 3 | " | 4-methylbenzyl | " |
| 10,11-dihydro-5-hydroxy-5H-dibenzo[a,d]cyclohepten-5-yl | " | " | " | " |

-continued

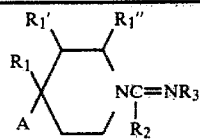

| Substituent (R₁, R₁', R₁") | Position of Substituent | R₂ | R₃ | A |
|---|---|---|---|---|
| 9-fluorenyl | " | " | " | " |
| α-(4-methoxyphenyl)benzyl | 4 | " | 4-chlorobenzyl | " |
| 4-chlorobenzyl | " | " | benzyl | " |
| diphenylmethyl | " | " | exo-2-norbornyl | " |
| α-(4-methylphenyl)benzyl | " | " | " | " |
| phenyl | " | " | " | phenyl |
| diphenylhydroxymethyl | " | " | " | H |
| diphenylmethyl | 3 | " | " | " |
| phenyl | 4 | " | " | " |
| 9-fluorenyl | 3 | " | " | " |
| benzyl | 4 | " | " | " |
| 10,11-dihydro-5H-dibenzo[a,d]cyclohepten-5-yl | " | " | " | " |
| diphenylmethyl | " | " | endo-2-norbornyl | " |
| α-(4-chlorophenyl)benzyl | " | " | " | " |
| α-(4-methylphenyl)-α-hydroxybenzyl | " | " | " | " |
| diphenylmethyl | 3 | " | " | " |
| 9-fluorenyl | " | " | " | " |
| 4-methoxyphenyl | 4 | " | " | " |
| 4-chlorobenzyl | " | " | " | " |
| diphenylmethyl | " | " | 1-decahydronaphthyl | " |
| α-(4-methoxyphenyl)benzyl | " | " | " | " |
| diphenylhydroxymethyl | " | " | " | " |
| α-(4-chlorophenyl)benzyl | 3 | " | " | " |
| 9-fluorenyl | " | " | " | " |
| 4-chlorophenyl | 4 | " | " | " |
| 4-methoxybenzyl | " | " | " | " |
| diphenylmethyl | " | " | 1-adamantyl | " |
| α-(4-chlorophenyl)benzyl | " | " | " | " |
| α-(4-methylphenyl)-α-hydroxybenzyl | " | " | " | " |
| diphenylmethyl | 3 | " | " | " |
| 9-fluorenyl | " | " | " | " |
| phenyl | 4 | " | " | " |
| benzyl | " | " | " | " |
| diphenylmethyl | " | " | 2-bicyclo[2.2.2]octyl | " |
| α-(4-methoxyphenyl)benzyl | " | " | " | " |
| diphenylhydroxymethyl | " | " | " | " |
| α-(4-chlorophenyl)benzyl | 3 | " | " | " |
| 9-fluorenyl | 4 | " | " | " |
| 4-chlorophenyl | " | " | " | " |
| 4-methoxybenzyl | " | " | " | " |
| diphenylmethyl | " | " | anti-7-norbornenyl | " |
| α-(4-methylphenyl)benzyl | " | " | " | " |
| diphenylhydroxymethyl | " | " | " | " |
| diphenylmethyl | 2 | " | " | " |
| α-(4-chlorophenyl)benzyl | 3 | " | " | " |
| phenyl | 4 | " | " | " |
| 9-fluorenyl | 3 | " | " | " |
| 4-methoxybenzyl | 4 | " | " | " |
| diphenylmethyl | " | " | endo-bicyclo[3.2.1]octyl | " |
| phenyl | " | " | " | phenyl |
| α-(4-chlorophenyl)benzyl | " | " | " | H |
| diphenylhydroxymethyl | " | " | " | " |
| diphenylmethyl | 3 | " | " | " |
| 9-fluorenyl | " | " | " | " |
| 4-chlorophenyl | 4 | " | " | " |
| benzyl | " | " | " | " |
| diphenylmethyl | " | " | 1-adamantylmethyl | " |
| α-(4-methylphenyl)benzyl | " | " | " | " |
| α-(4-chlorophenyl)-α-hydroxybenzyl | " | " | " | " |
| diphenylmethyl | 3 | " | " | " |
| 9-fluorenyl | " | " | " | " |
| 4-methoxyphenyl | 4 | " | " | " |
| 4-chlorobenzyl | " | " | " | " |
| diphenylmethyl | " | n-butyl | H | " |
| α-(4-methoxyphenyl)benzyl | " | " | " | " |
| diphenylhydroxymethyl | " | " | " | " |
| diphenylmethyl | 3 | " | " | " |

-continued

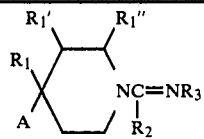

| Substituent (R₁, R₁', R₁'') | Position of Substituent | R₂ | R₃ | A |
|---|---|---|---|---|
| 9-fluorenyl | " | " | " | " |
| phenyl | 4 | " | " | " |
| 4-chlorobenzyl | " | " | " | " |
| diphenylmethyl | " | " | —C₂H₅ | " |
| phenyl | " | " | " | phenyl |
| α-(4-methoxyphenyl)benzyl | " | " | " | H |
| α-(4-chlorophenyl)-α-hydroxybenzyl | " | " | " | " |
| diphenylmethyl | 2 | " | " | " |
| α-(4-chlorophenyl)benzyl | 3 | " | " | " |
| 9-fluorenyl | " | " | " | " |
| 4-methoxyphenyl | 4 | " | " | " |
| benzyl | " | " | " | " |
| diphenylmethyl | " | " | —(CH₂)₇CH₃ | " |
| α-(4-chlorophenyl)benzyl | " | " | " | " |
| diphenylhydroxymethyl | " | " | " | " |
| diphenylmethyl | 3 | " | " | " |
| 9-fluorenyl | " | " | " | " |
| phenyl | 4 | " | " | " |
| benzyl | " | " | " | " |
| diphenylmethyl | " | " | —(CH₂)₁₄CH₃ | " |
| α-(4-methylphenyl)benzyl | " | " | " | " |
| diphenylhydroxymethyl | " | " | " | " |
| α-(4-chlorophenyl)benzyl | 3 | " | " | " |
| 9-fluorenyl | " | " | " | " |
| 10,11-dihydro-5-hydroxy-5H-dibenzo[a,d]cyclohepten-5-yl | " | " | " | " |
| 4-methoxyphenyl | 4 | " | " | " |
| 4-chlorobenzyl | " | " | " | " |
| diphenylmethyl | " | " | —CH₂CH=CH₂ | " |
| α-(4-chlorophenyl)benzyl | " | " | " | " |
| diphenylhydroxymethyl | " | " | " | " |
| α-(4-chlorophenyl)benzyl | 3 | " | " | " |
| 9-fluorenyl | " | " | " | " |
| 4-chlorophenyl | 4 | " | " | " |
| benzyl | " | " | " | " |
| diphenylmethyl | " | " | —(CH₂)₄CH=CHC₂H₅ | " |
| 5-hydroxy-5H-dibenzo[a,d]cyclohepten-5-yl | " | " | " | " |
| α-(4-methylphenyl)benzyl | " | " | " | " |
| α-(4-methoxyphenyl)-α-hydroxybenzyl | " | " | " | " |
| diphenylmethyl | 3 | " | " | " |
| 9-fluorenyl | " | " | " | " |
| phenyl | 4 | " | " | " |
| 4-chlorobenzyl | " | " | " | " |
| diphenylmethyl | " | " | cis-(CH₂)₅CH=CH(CH₂)₁₀CH₃ | " |
| α-(4-methylphenyl)benzyl | " | " | " | " |
| diphenylhydroxymethyl | " | " | " | " |
| α-(4-chlorophenyl)benzyl | 3 | " | " | " |
| 9-fluorenyl | " | " | " | " |
| phenyl | 4 | " | " | " |
| 4-methoxybenzyl | " | " | " | " |
| diphenylmethyl | " | " | —CH₂C≡CH | " |
| α-(4-methylphenyl)benzyl | " | " | " | " |
| diphenylhydroxymethyl | " | " | " | " |
| 10,11-dihydro-5H-dibenzo[a,d]cyclohepten-5-yl | " | " | " | " |
| diphenylmethyl | 3 | " | " | " |
| 9-fluorenyl | " | " | " | " |
| 4-methoxyphenyl | 4 | " | " | " |
| benzyl | " | " | " | " |
| diphenylmethyl | " | " | —(CH₂)₆C≡CH | " |
| α-(4-chlorophenyl)benzyl | " | " | " | " |
| phenyl | " | " | " | phenyl |
| α-(4-methoxyphenyl)-α-hydroxybenzyl | " | " | " | H |
| α-(4-chlorophenyl)benzyl | 3 | " | " | " |
| 9-fluorenyl | " | " | " | " |
| phenyl | 4 | " | " | " |
| 4-methoxybenzyl | " | " | " | " |

-continued

| Substituent (R₁, R₁', R₁") | Position of Substituent | R₂ | R₃ | A |
|---|---|---|---|---|
| diphenylmethyl | " | " | benzyl | " |
| α-(4-methylphenyl)benzyl | " | " | 4-chlorobenzyl | " |
| α-(4-chlorophenyl)-α-hydroxybenzyl | " | " | 4-methylbenzyl | " |
| diphenylhydroxymethyl | 2 | " | " | " |
| diphenylmethyl | 3 | " | 4-methoxybenzyl | " |
| 9-fluorenyl | " | " | " | " |
| phenyl | 4 | " | benzyl | " |
| 4-methoxybenzyl | " | " | 4-methylbenzyl | " |
| diphenylmethyl | " | " | phenethyl | " |
| α-(4-methoxyphenyl)benzyl | " | " | " | " |
| diphenylhydroxymethyl | " | " | " | " |
| diphenylmethyl | 3 | " | " | " |
| 9-hydroxy-9-fluorenyl | 4 | " | " | " |
| phenyl | " | " | " | " |
| 4-chlorobenzyl | " | " | " | " |
| diphenylmethyl | " | " | exo-2-norbornyl | " |
| α-(4-methylphenyl)benzyl | " | " | " | " |
| diphenylhydroxymethyl | " | " | " | " |
| α-(4-chlorophenyl)benzyl | 3 | " | " | " |
| 9-fluorenyl | " | " | " | " |
| 4-methoxyphenyl | 4 | " | " | " |
| benzyl | " | " | " | " |
| diphenylmethyl | " | " | endo-2-norbornyl | " |
| α-(4-chlorophenyl)benzyl | " | " | " | " |
| α-(4-methylphenyl)-α-hydroxybenzyl | " | " | " | " |
| diphenylmethyl | 3 | " | " | " |
| 9-fluorenyl | " | " | " | " |
| phenyl | 4 | " | " | " |
| 4-methoxybenzyl | " | " | " | " |
| diphenylmethyl | " | " | 1-decahydronaphthyl | " |
| α-(4-chlorophenyl)benzyl | " | " | " | " |
| α-(4-methoxyphenyl)-α-hydroxybenzyl | " | " | " | " |
| phenyl | " | " | " | phenyl |
| α-(4-chlorophenyl)benzyl | 3 | " | " | H |
| 9-fluorenyl | " | " | " | " |
| phenyl | 4 | " | " | " |
| benzyl | " | " | " | " |
| diphenylmethyl | " | " | 1-adamantyl | " |
| α-(4-methoxyphenyl)benzyl | " | " | " | " |
| diphenylhydroxymethyl | " | " | " | " |
| diphenylmethyl | 3 | " | " | " |
| 9-fluorenyl | " | " | " | " |
| 4-chlorophenyl | 4 | " | " | " |
| 4-chlorobenzyl | " | " | " | " |
| diphenylmethyl | " | " | 2-bicyclo[2.2.2]octyl | " |
| α-(4-methylphenyl)benzyl | " | " | " | " |
| α-(4-chlorophenyl)-α-hydroxybenzyl | " | " | " | " |
| α-(4-chlorophenyl)benzyl | 3 | " | " | " |
| 9-fluorenyl | " | " | " | " |
| phenyl | 4 | " | " | " |
| 4-methoxybenzyl | " | " | " | " |
| diphenylmethyl | " | " | anti-7-norbornenyl | " |
| α-(4-methylphenyl)benzyl | " | " | " | " |
| diphenylhydroxymethyl | " | " | " | " |
| diphenylmethyl | 3 | " | " | " |
| 9-fluorenyl | " | " | " | " |
| diphenylmethyl | 2 | " | " | " |
| 4-methoxyphenyl | 4 | " | " | " |
| 4-chlorobenzyl | " | " | " | " |
| diphenylmethyl | " | " | endo-bicyclo[3.2.1]octyl | " |
| α-(4-methoxyphenyl)benzyl | " | " | " | " |
| α-(4-methylphenyl)-α-hydroxybenzyl | " | " | " | " |
| α-(4-chlorophenyl)benzyl | 3 | " | " | " |
| 9-fluorenyl | " | " | " | " |
| phenyl | 4 | " | " | " |
| 4-methoxybenzyl | " | " | " | " |

-continued

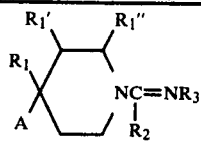

| Substituent ($R_1$, $R_1'$, $R_1''$) | Position of Substituent | $R_2$ | $R_3$ | A |
|---|---|---|---|---|
| diphenylmethyl | " | " | 1-adamantylmethyl | " |
| α-(4-methoxyphenyl)benzyl | " | " | " | " |
| diphenylhydroxymethyl | " | " | " | " |
| diphenylmethyl | 3 | " | " | " |
| 9-fluorenyl | " | " | " | " |
| phenyl | 4 | " | " | " |
| benzyl | " | " | " | " |
| α-(1,4-biphenyl)benzyl | " | H | H | " |
| α-(1,4-biphenyl)benzyl | " | $CH_3$ | —$(CH_2)_7CH_3$ | " |
| α-(1,4-biphenyl)benzyl | " | n-butyl | phenethyl | " |
| 2,2-diphenylethyl | " | H | H | " |
| 2,2-diphenylethyl | " | $CH_3$ | —$(CH_2)_7CH_3$ | " |
| 2,2-diphenylethyl | " | n-butyl | phenethyl | " |
| 4,4-diphenyl-n-butyl | " | H | H | " |
| 4,4-diphenyl-n-butyl | " | $CH_3$ | —$(CH_2)_7CH_3$ | " |
| 4,4-diphenyl-n-butyl | " | n-butyl | phenethyl | " |
| diphenylmethyl | " | H | diphenylmethyl | " |
| phenyl | 3 | $CH_3$ | " | " |
| 9-fluorenyl | 4 | n-butyl | " | " |
| 4-chlorobenzyl | " | H | 3,3-diphenyl-n-propyl | " |
| diphenylmethyl | 3 | $CH_3$ | " | " |
| diphenylhydroxymethyl | 4 | n-butyl | " | " |
| phenyl(octyl)methyl | " | H | H | " |
| 10,11-dihydro-5H-dibenzo[a,d]cyclohepten-5-yl | 2 | " | —$(CH_2)_7CH_3$ | " |
| 5H-dibenzo[a,d]cyclohepten-5-yl | " | " | " | " |
| phenyl(hexyl)methyl | 4 | " | $(CH_2)_6C{\equiv}CH$ | " |
| phenyl(hexyl)methyl | " | methyl | —$(CH_2)_4CH{=}CHCH_2CH_3$ | " |
| 10,11-dihydro-5H-dibenzo[a,d]cyclohepten-5-yl | 2 | " | —$(CH_2)_6C{\equiv}CH$ | " |
| 5H-dibenzo[a,d]cyclohepten-5-yl | " | " | " | " |
| 10,11-dihydro-5H-dibenzo[a,d]cyclohepten-5-yl | " | n-butyl | —$CH_2C{\equiv}H$ | " |
| 5H-dibenzo[a,d]cyclohepten-5-yl | " | " | " | " |
| phenyl(octyl)methyl | 4 | " | phenethyl | " |

EXAMPLE XVIII

Following the procedure of either Example I or Example III, but substituting for the ethyl formimidate hydrochloride and 4-diphenylmethylpiperidine or N-formyl-4-diphenylmethylpiperidine and ethylamine, respectively, used therein, equivalent amounts of the appropriate starting materials such as described in Examples XIII and XVI, there are prepared the following:

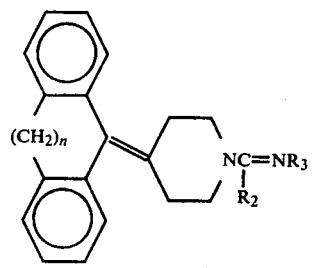

| Position of Substituent | n | $R_2$ | $R_3$ |
|---|---|---|---|
| 3 | 0 | H | H |

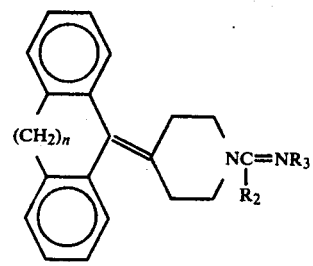

| Position of Substituent | n | $R_2$ | $R_3$ |
|---|---|---|---|
| 3 | 0 | H | n-octyl |
| 3 | 0 | H | n-dodecyl |
| 4 | 0 | H | n-hexadecyl |
| 4 | 0 | $CH_3$ | n-octyl |
| 4 | 0 | n-butyl | n-octyl |
| 3 | 1 | H | H |
| 3 | 1 | H | n-octyl |
| 3 | 1 | H | n-dodecyl |
| 4 | 1 | H | n-hexadecyl |
| 4 | 1 | $CH_3$ | n-octyl |
| 4 | 1 | n-butyl | n-octyl |
| 3 | 2 | H | H |
| 3 | 2 | H | n-octyl |
| 3 | 2 | H | n-dodecyl |

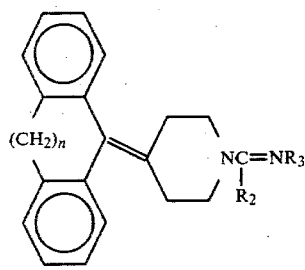

| Position of Substituent | n | $R_2$ | $R_3$ |
|---|---|---|---|
| 4 | 2 | H | n-hexadecyl |
| 4 | 2 | $CH_3$ | n-octyl |
| 4 | 2 | n-butyl | n-octyl |

EXAMPLE XIX

Following the procedure of either Example I or Example III, but substituting for the ethyl formimidate hydrochloride and 4-diphenylmethylpiperidine or N-formyl- 4-diphenylmethylpiperidine and ethylamine, respectively, used therein, equivalent amounts of the appropriate starting materials such as described in Examples XIV and XVI, there are prepared the following:

| $R_2$ | $R_3$ |
|---|---|
| H | H |
| H | n-octyl |
| H | n-dodecyl |
| H | n-hexadecyl |
| $CH_3$ | n-octyl |
| n-butyl | n-octyl |
| H | H |
| H | n-octyl |
| H | n-dodecyl |
| H | n-hexadecyl |
| $CH_3$ | n-octyl |
| n-butyl | n-octyl |
| H | H |
| H | n-octyl |
| H | n-dodecyl |
| H | n-hexadecyl |
| $CH_3$ | n-octyl |
| n-butyl | n-octyl |

EXAMPLE XX

Following the procedure of either Example I or Example III, but substituting for the ethyl formimidate hydrochloride and 4-diphenylmethylpiperidine or N-formyl-4-diphenylmethylpiperidine and ethylamine, respectively, used therein, equivalent amounts of the appropriate starting materials such as described in Examples XV and XVI, there are prepared the following:

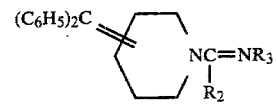

| Position of Substituent | n | $R_2$ | $R_3$ |
|---|---|---|---|
| 2 | 0 | H | H |
| 2 | 0 | H | n-octyl |
| 3 | 0 | H | n-dodecyl |
| 3 | 0 | H | n-hexadecyl |
| 4 | 0 | $CH_3$ | n-octyl |
| 4 | 0 | n-butyl | n-octyl |
| 2 | 1 | H | H |
| 2 | 1 | H | n-octyl |
| 3 | 1 | H | n-dodecyl |
| 3 | 1 | H | n-hexadecyl |
| 4 | 1 | $CH_3$ | n-octyl |
| 4 | 1 | n-butyl | n-octyl |
| 2 | 2 | H | H |
| 2 | 2 | H | n-octyl |
| 3 | 2 | H | n-dodecyl |
| 3 | 2 | H | n-hexadecyl |
| 4 | 2 | $CH_3$ | n-octyl |
| 4 | 2 | n-butyl | n-octyl |

EXAMPLE XXI

N-[4-(Diphenylmethyl)-1-piperidinyl]methylene benzenebutanamine (E)-2-Butenedioate Hydrate A mixture of 4.40 g (0.016 mole) of N-formyl-4-(diphenylmethyl)piperidine and 1.47 ml (2.00 g, 0.015 mole) of dimethyl sulfate was heated in a steam bath for three hours at 100° C. under anhydrous conditions until homogeneous. The mixture was cooled, dissolved in 30 ml of methylene chloride and treated with 2.50 ml (2.36 g, 0.016 mole) of phenylbutylamine. The resulting solution was stirred for three hours and treated with 6 ml 3 N sodium hydroxide solution with vigorous stirring at 0°. The organic layer was separated, dried over potassium carbonate, filtered and evaporated to an oil. This material was dissolved in isopropanol, treated with 1.84 g of fumaric acid and cooled. There was filtered off a white crystalline solid which as recrystallized from ethanol to give N-[4-(diphenylmethyl)-1-piperidinyl]-methylene benzenebutanamine (E)-2-butenedioate hydrate as a white crystalline solid, m.p. 207°–208.5° C.

EXAMPLE XXII 4-(Diphenylmethyl)-1-[1-(octylimino)ethyl]-piperidine Monoperchlorate A mixture of the fluoroborate salt of N-octylacetimidic acid ethyl ester (generated from 5.68 g [0.04 mole] of boron trifluoride etherate, 2.77 g [0.03 mole] of epichlorohydrin, and 5,80 g [0.034 mole] of N-octyl acetamide) and 50 ml of ether was treated with 4 ml (2.92 g, 0.029 mole) of triethyl amine. Filtration and evaporation of the filtrate afforded a liquid residue which was dissolved in 120 ml dry toluene. To this solution was added 6.00 g (0.024 mole) of glacial acetic acid and the resulting solution was stirred at 50° C. over 4A molecular sieves under a nitrogen atmosphere for four days. The reaction mixture was cooled and neutralized by shaking with 3 N sodium hydroxide solution. The organic layer was separated, dried over $K_2CO_3$, filtered and stripped to an oil which as distilled. The pot residue was dissolved in ether and perchloric acid and methanol added. Cooling the solution produced a solid fraction. Filtration afforded a crystalline solid which was recrystallized three times from methanol to give 4-(Diphenylmethyl)-1-[1-(octylimino)-ethyl]piperidine Monoperchlorate as a white crystalline solid, m.p. 119°–121.5° C.

EXAMPLE XXIII

α-(4-Methylphenyl)-α-phenyl-4-pyridine Methanol

A solution of 0.05 mole of 4-methylphenyl magnesium bromide in 500 ml of anhydrous ether was treated with 4-benzoylpyridine in 500 ml anhydrous ether. After stirring the resulting mixture for 1.5 hours at 25°, an aqueous solution of ammonium chloride was added causing a solid to form which was filtered. Recrystallization of this material from 95% ethanol afforded the desired α-(4-methylphenyl)-α-phenyl-4-pyridine methanol, m.p. 192°–195° C. The corresponding 4-chlorophenyl (m.p. 198°–202° C.) and 4-methoxyphenyl (m.p. 204°–206° C.) derivatives were also prepared by the same method, using equivalent amounts of the appropriate starting materials.

EXAMPLE XXIV

α-(4-Methylphenyl)-α-phenyl-4-piperidine

A solution of 25.0 g (0.09 mole) α-(4-methylphenyl)-α-phenyl-4-pyridine methanol, 55 ml of 47–51% hydriodic acid and 180 ml of acetic acid was refluxed overnight, cooled, and poured into aqueous sodium bisulfite. This solution was made basic with sodium hydroxide and extracted with methylene chloride. From the organic layer there was isolated an oil which was reduced at 40 psi over platinum oxide at 60°–65° C. in acetic acid following the method of U.S. Pat. No. 3,267,108. The excess acid was removed and the residue made basic to give α-(4-methylphenyl)-α-phenyl-4-piperidine which was characterized as its fumarate salt, m.p. 157.5°–161.5° C. (Hoover). The corresponding 4-chlorophenyl (m.p. 175°–178° C.; fumarate salt) and 4-methoxyphenyl (m.p. 94°–98° C.; free base) derivatives were also prepared by the same method, using equivalent amounts of the appropriate starting materials.

EXAMPLE XXV

α-(1,4'-Biphenyl)yl-α-phenyl-4-pyridinemethanol

A solution of 111.0 g (0.50 mole) of 4-biphenyl bromide in 200 ml of dry tetrahydrofuran (THF) was added slowly to a mixture of 12.10 g (0.5 gram-atom) of magnesium, 2 ml of ethylenedibromide and 200 ml of THF at such a rate as to maintain reflux. After addition the mixture was refluxed for 0.5 hours, cooled and treated over 0.5 hours with a solution of 82.3 g (0.45 mole) of 4-benzoylpyridine in 600 ml THF. The resulting slurry was stirred 0.5 hours at 25° C. and treated with 1000 ml 20% ammonium chloride solution. The organic layer was separated, filtered, the filtrate dried, filtered and stripped. The residue was triturated with ether and filtered. This solid was recrystallized from ethanol, chloroform, and finally toluene to give α-(1,4'-biphenyl)-yl-α-phenyl-4-pyridinemethanol as a white solid, m.p. after drying in vacuo at 70° C.; 173.5°–175.5° C.

EXAMPLE XXVI

α-(1,4'-Biphenyl)yl-α-phenyl-4-piperidinemethanol

A solution of 10.00 g (0.030 mole) of α-(1,4'-biphenyl)yl-α-phenyl-4-pyridine and 160 ml of acetic acid was hydrogenated in the presence of platinum oxide (1.0 g) at 25–35 psi at 70°–90° on a Paar shaker. After hydrogen uptake ceased, the mixture was filtered through dicalite and evaporated to a solid residue. This residue was slurried in water, made basic with 3 N NaOh and extracted with chloroform. The chloroform layer was dried over potassium carbonate, filtered through dicalite and evaporated. The residue was dissolved in toluene and cooled. The resulting solid was filtered and recrystallized from toluene to give α-(1,4'-biphenyl)yl-α-phenyl-4-piperidinemethanol as a white solid; m.p. 185°–186.5° C.

EXAMPLE XXVII 9-(4'-piperidinyl)-9-fluorenol

A solution of 13.0 g (0.05 mole) of 9-(4'-pyridyl)-9-fluorenol in 200 of glacial acetic acid was hydrogenated over 0.8 g of platinum oxide at 40 psi. The mixture was filtered, stripped, and the residue made basic affording 9-(4'-piperidinyl)-9-fluorenol.

EXAMPLE XXVIII

4-Fluorenylidenepiperidine

A suspension of 13.0 g (0.05 mole) of 9-(4'-piperidinyl)-9-fluorenol in 70 ml of 48% sulfuric acid was heated on a steam bath for seven hours and poured on to ice. The resulting solid was filtered, made basic with sodium hydroxide solution and extracted with methylene chloride. The organic layer was separated, dried over potassium carbonate, filtered and stripped to give 4-fluorenylidenepiperidine.

EXAMPLE XXIX 9-(4'-Pyridyl)fluorene

A solution of 1.35 g (0.005 mole) of α, α-diphenyl-4-pyridine methanol in 18.5 ml of 97% formic acid was treated dropwise with 8 ml of concentrated sulfuric acid. The reaction was refluxed ten minutes, cooled and made basic with 6 N sodium solution causing a solid to separate. This material was filtered and recrystallized from methanol to give 9-(4'-pyridyl)fluorene, m.p. 141°–143° C. (Hoover).

EXAMPLE XXX 9-(4'-Piperidyl)fluorene fumarate

A solution of 54.75 g (0.225 mole) of 9-(4'-pyridyl)-fluorene in 600 ml of acetic acid was hydrogenated over 5.0 g of platinum oxide at 40 psi and 25° C. The mixture was filtered, stripped and made basic, affording 9-(4'-piperidyl)fluorene, which was crystallized as the fumarate salt, m.p. 228°–230° C. (dec).

What is claimed is:

1. A member selected from the group consisting of a substituted N-iminomethylpiperidine of formula (I):

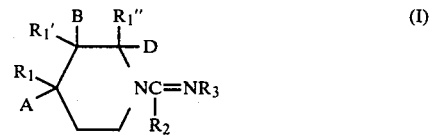

and the corresponding non-toxic acid addition salts thereof, wherein:

$R_1$ taken individually is a member selected from the group consisting of hydrogen; phenyl; phenyl substituted with from one to three members each selected from the group consisting of loweralkyl, loweralkoxy, hydroxy and halo; phenyl($C_1$-$C_4$)-loweralkyl; 1-phenyl($C_7$-$C_9$)loweralkyl; phenyl($C_1$-$C_4$) loweralkyl and 1-phenyl($C_7$-$C_9$)loweralkyl in which said phenyl is substituted with from one to three members each selected from the group consisting of loweralkyl, loweralkoxy, hyroxy, halo, and phenyl, provided that no more than one member is phenyl; diphenyl($C_1$-$C_4$)loweralkyl; diphenyl($C_1$-$C_4$)loweralkyl wherein at least one of said phenyls is substituted with from one to three members each selected from the group consisting of loweralkyl, loweralkoxy, halo, hydroxy, and phenyl, provided that no more than one member is phenyl; diphenylhydroxymethyl; diphenylhydroxymethyl wherein at least one of said phenyls is substituted with from one to three members each selected from the group consisting of loweralkyl, loweralkoxy, hydroxy, halo, and phenyl, provided that no more than one member is phenyl; and radicals of formulae:

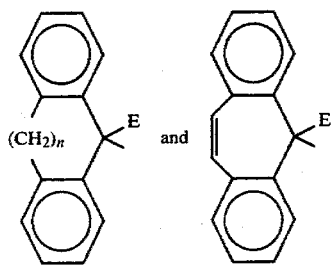

wherein n is 0, 1, or 2 and E is H or OH;

A taken individually is a member selected from hydrogen, acetyl, and phenyl, provided that when A is acetyl or phenyl, $R_1$ is a member selected from the group consisting of phenyl of phenyl substituted with from one to three members each selected from the group consisting of loweralkyl, loweralkoxy, hydroxy and halo;

$R_1$ and A taken together is a member selected from the group consisting of benzhydrylidene and radicals of formulae:

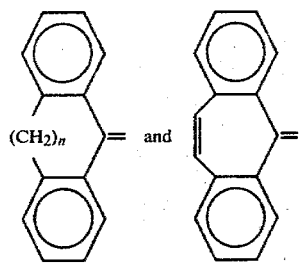

wherein n is 0, 1, or 2;

$R_1'$ taken individually is a member selected from the group consisting of hydrogen; methyl; diphenylmethyl; diphenylmethyl wherein at least one of the phenyl groups is substituted with from one to three members each selected from the group consisting of loweralkyl, loweralkoxy, hydroxy, halo; and phenyl, provided that no more than one member is phenyl; diphenylhydroxymethy; diphenylhydroxymethyl wherein at least one of said phenyls is substituted with from one to three members each selected from the group consisting of loweralkyl, loweralkoxy, halo, hydroxy, and phenyl, provided that no more than one member is phenyl; and a radical of formula:

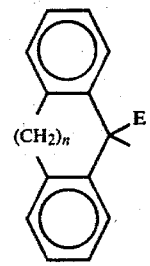

wherein n is 0, 1, or 2 and E is H or OH;

B taken individually is hydrogen;

$R_1'$ and B taken together is a member selected from the group consisting of benzhydrylidene and a radical of formula

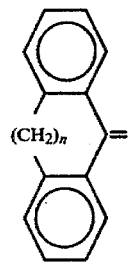

wherein n is 0, 1, or 2

$R_1''$ taken individually is a member selected from the group consisting of hydrogen, diphenylmethyl; diphenylmethyl wherein at least one of said phenyls is substituted with from one to three members each selected from the group consisiting of loweralkyl, loweralkoxy, halo, hydroxy, and phenyl, provided that no more than one member is phenyl; diphenylhydroxymethyl: diphenylhydroxymethyl wherein at least one of said phenyls is substituted with from one to three members each selected from the group consisting of loweralkyl, loweralkoxy, hydroxy, halo, and phenyl, provided that no more than one member is phenyl; and radicals of formulae:

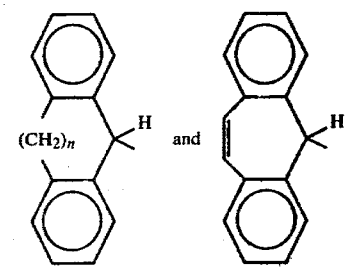

wherein n is 0, 1, or 2;

D taken individually is hydrogen;

$R_1''$ and D taken together is benzhydrylidene;

$R_2$ is a member selected from the group consisting of hydrogen and $C_1$-$C_4$ loweralkyl; and $R_3$ is a member selected from the group consisting of hydrogen; alkyl; cycloalkyl; phenylloweralkyl; phenylloweralkyl in which said phenyl is substituted with from one to three members each selected from the group consisting of loweralkyl, loweralkyl, hydroxy, and halo; diphenyl ($C_1$–$C_4$) loweralkyl; diphenyl($C_1$–$C_4$) loweralkyl wherein at least one of said phenyls is substituted with from one to three members each selected from the group consisting of loweralkyl, loweralkoxy, halo, hydroxy, and phenyl, provided that no more than one member is phenyl; alkenyl; and alkynyl;

provided that at least one of said $R_1$, $R_1'$, and $R_1''$ is other than hydrogen and further provided that when $R_1''$ is other than hydrogen $R_1$, $R_1'$, and A are each hydrogen; when $R_1'$ is hydrogen only one of $R_1$ and $R_1''$ is other than hydrogen; when $R_1'$ is methyl $R_1$ is other than hydrogen and $R_1''$ is hydrogen; and when $R_1'$ is other than hydrogen or methyl $R_1$, $R_1''$ and A are each hydrogen.

2. The substituted N-iminomethylpiperidine of claim 1 wherein:

$R_1$ is a member selected from the group consisting of phenyl; phenyl substituted with from one to three members each selected from the group consisting of loweralkyl, loweralkoxy, halo, and phenyl, provided that no more than one member is phenyl; phenyl ($C_1$–$C_4$) loweralkyl; phenyl ($C_1$–$C_4$) loweralkyl in which said phenyl is substituted with from one to three members each selected from the group consisting of loweralkyl, loweralkoxy, and halo; diphenyl ($C_1$–$C_4$) loweralkyl and diphenyl ($C_1$–$C_4$) loweralkyl wherein at least one of said phenyls is substituted with from one to three members each selected from the group consisting of loweralkyl, loweralkoxy, halo, and phenyl, provided that no more than one member is phenyl;

$R_2$ is a member selected from the group consisting of hydrogen; and methyl;

$R_3$ is a member selected from the group consisting of hydrogen, alkyl; cycloalkyl; phenylloweralkyl; phenylloweralkyl in which said phenyl is substituted with from one to three members each selected from the group consisting of loweralkyl, loweralkoxy, and halo; alkenyl; and alkynyl; and $R_1'$, $R_1''$, A, B, and D are each hydrogen.

3. The substituted N-iminomethylpiperidine of claim 2 wherein:

$R_1$ is a member selected from the group consisting of diphenylmethyl and diphenylmethyl wherein at least one of said phenyls is substituted with from one to three members each selected from the group consisting of loweralkyl, loweralkoxy, and halo;

$R_2$ is hydrogen;

$R_3$ is a member selected from the group consisting of hydrogen; alkyl; phenylloweralkyl; phenylloweralkyl in which said phenyl is substituted with from one to three members each selected from the group consisting of loweralkyl, loweralkoxy; and halo; alkenyl; and alkynyl; and $R_1'$, $R_1''$, A, B, and D are each hydrogen.

4. The substituted N-iminomethylpiperidine of claim 3 wherein:

$R_1$ is a member selected from the group consisting of diphenylmethyl and diphenylmethyl wherein one of said phenyls is substituted in the para-position with a member selected from the group consisting of loweralkyl, loweralkoxy, and halo;

$R_2$ is hydrogen;

$R_3$ is a member selected from the group consisting of hydrogen; straight chain alkyl; and phenylloweralkyl; and $R_1'$, $R_1''$, A, B, and D are each hydrogen.

5. A member selected from the group consisting of 4-diphenylmethyl-1-iminomethylpiperidine and the non-toxic acid addition salts thereof.

6. A member selected from the group consisting of 4-(diphenylmethyl)-1-[(isopropylimino)methyl]piperidine and the non-toxic acid addition salts thereof.

7. A member selected from the group consisting of 1-[N-(benzyl)iminomethyl]-4-diphenylmethylpiperidine and the non-toxic acid addition salts thereof.

8. A member selected from the group consisting of 1-[N-(phenethyl)iminomethyl]-4-diphenylmethylpiperidine and the non-toxic acid addition salts thereof.

9. A member selected from the group consisting of 1-[N-(n-decyl)iminomethyl]-4-diphenylmethylpiperidine and the non-toxic acid additions salts thereof.

10. A member selected from the group consisting of 4-(diphenylmethyl)-1-[(octylimino)methyl]piperidine and the non-toxic acid addition salts thereof.

11. A member selected from the group consisting of 4-(diphenylmethyl)-1-[(ethylimino)methyl]piperidine and the non-toxic acid addition salts thereof.

12. A member selected from the group consisting of 1-[N-(n-butyl)iminomethyl]-4-diphenylmethylpiperidine and the non-toxic acid addition salts thereof.

13. A member selected from the group consisting of 4-(diphenylmethyl)-1-[(hexylimino)methyl]piperidine and the non-toxic acid addition salts thereof.

14. A member selected from the group consisting of 4-(diphenylmethyl)-1-[(heptylimino)methyl]piperidine and the non-toxic acid addition salts thereof.

15. A member selected from the group consisting of 4-(diphenylmethyl)-1-[(t-octylimino)methyl]piperidine and the non-toxic acid addition salts thereof.

16. A member selected from the group consisting of 4-(diphenylmethyl)-1-[(nonylimino)methyl]piperidine and the non-toxic acid addition salts thereof.

17. A member selected from the group consisting of 4-(diphenylmethyl)-1-[(dodecylimino)methyl]piperidine and the non-toxic acid addition salts thereof.

18. A member selected from the group consisting of 1-[(1-adamantylimino)methyl]-4-(diphenylmethyl)-piperidine and the non-toxic acid addition salts thereof.

19. A member selected from the group consisting of 1-[(4-chlorobenzylimino)methyl]-4-(diphenylmethyl)-piperidine and the non-toxic acid addition salts thereof.

20. A member selected from the group consisting of 1-[(allylimino)methyl]-4-diphenylmethyl)piperidine and the non-toxic acid addition salts thereof.

21. A member selected from the group consisting of 4-(diphenylmethyl)-1-[(2-propynylimino)methyl]-piperidine and the non-toxic acid addition salts thereof.

22. A member selected from the group consisting of 4-(diphenylmethyl)-1-[(9-octadecen-1-ylimino)methyl]-piperidine and the non-toxic acid addition salts thereof.

23. A member selected from the group consisting of 4-(diphenylmethyl)-1-[ethyl(imino)methyl]piperidine and the non-toxic acid addition salts thereof.

24. A member selected from the group consisting of 4-[1-(4-methoxyphenyl)benzyl]-1-iminomethylpiperidine and the non-toxic acid addition salts thereof.

25. A member selected from the group consisting of 4[1-(4-methoxyphenyl)benzyl]-1-[(octylimino)methyl]-piperidine and the non-toxic acid addition salts thereof.

26. A member selected from the group consisting of 4[1-(4-chlorophenyl)benzyl]-1-iminomethylpiperdine and the non-toxic acid addition salts thereof.

27. A member selected from the group consisting of 4(9-fluorenyl)-1-[(octylimino)methyl]piperidine and the non-toxic acid addition salts thereof.

28. A member selected from the group consisting of 4[1-methylphenyl)benzyl]-1-[(octylimino)methyl]-piperidine and the non-toxic acid addition salts thereof.

29. A member selected from the group consisting of 4-(diphenylmethyl)-1-[methyl(octylimino)methyl]-piperidine and the non-toxic acid addition salts thereof.

30. A member selected from the group consisting of N-[4-(diphenylmethyl)-1-piperidinyl]methylene benzenebutanamine and the non-toxic acid addition salts thereof.

31. A member selected from the group consisting of 4-acetyl-1-(iminomethyl)-4-phenylpiperidine and the non-toxic acid addition salts thereof.

32. A member selected from the group consisting of 4-benzhydrylidene-1-[(octylimino)methyl]piperidine and the non-toxic acid addition salts thereof.

33. A member selected from the group consisting of 3-(diphenylmethyl)-1-[(octylimino)methyl]piperidine and the non-toxic acid addition salts thereof.

34. A member selected from the group consisting of 3-(diphenylmethyl)-1-(iminomethyl)piperidine and the non-toxic acid addition salts thereof.

35. A member selected from the group consisting of 4-(diphenylhydroxymethyl)-1-[(octylimino)methyl]-piperidine and the non-toxic addition salts thereof.

36. A member selected from the group consisting of 4-[(4-hydroxyphenyl)phenylmethyl]-1-[(octylimino)-methyl]piperidine and the non-toxic addition salts thereof.

* * * * *